US010526667B2

(12) United States Patent
Leckie et al.

(10) Patent No.: US 10,526,667 B2
(45) Date of Patent: *Jan. 7, 2020

(54) HEPATITIS B VIRUS TYPING AND RESISTANCE ASSAY

(71) Applicant: Abbott Molecular Inc., Des Plaines, IL (US)

(72) Inventors: Gregor W. Leckie, Des Plaines, IL (US); Reuben J. Ofsaiof, Des Plaines, IL (US); Roy M. Vijesurier, Des Plaines, IL (US); Hong Wang, Des Plaines, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 907 days.

This patent is subject to a terminal disclaimer.

(21) Appl. No.: 14/701,368

(22) Filed: Apr. 30, 2015

(65) Prior Publication Data

US 2015/0259755 A1  Sep. 17, 2015

Related U.S. Application Data

(63) Continuation of application No. 13/774,960, filed on Feb. 22, 2013, now Pat. No. 9,045,803.

(60) Provisional application No. 61/605,029, filed on Feb. 29, 2012.

(51) Int. Cl.
*C12Q 1/70* (2006.01)
*C12Q 1/68* (2018.01)

(52) U.S. Cl.
CPC ............... *C12Q 1/706* (2013.01); *C12Q 1/68* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,458,066 | A | 7/1984 | Caruthers et al. |
| 5,210,015 | A | 5/1993 | Gelfand et al. |
| 5,686,243 | A | 11/1997 | Royer et al. |
| 5,723,591 | A | 3/1998 | Livak et al. |
| 5,830,711 | A | 11/1998 | Barany et al. |
| 6,027,889 | A | 2/2000 | Barany et al. |
| 6,027,998 | A | 2/2000 | Pham et al. |
| 6,262,490 | B1 | 7/2001 | Hsu et al. |
| 6,605,451 | B1 | 8/2003 | Marmaro et al. |
| 6,670,461 | B1 | 12/2003 | Wengel et al. |
| 6,709,812 | B1 | 3/2004 | Stuyver et al. |
| 6,770,748 | B2 | 8/2004 | Imanishi et al. |
| 6,794,499 | B2 | 9/2004 | Wengel et al. |
| 7,015,317 | B2 | 3/2006 | Mullen et al. |
| 7,118,910 | B2 | 10/2006 | Unger et al. |
| 9,045,803 | B2 | 6/2015 | Leckie et al. |
| 2004/0029110 | A1* | 2/2004 | Stuyver ............. C12Q 1/706 435/5 |

FOREIGN PATENT DOCUMENTS

| | | |
|---|---|---|
| WO | WO/1997/031256 | 8/1997 |
| WO | WO/1998/003673 | 1/1998 |
| WO | WO/2000/056927 | 9/2000 |
| WO | WO/2001/004358 | 1/2001 |
| WO | WO/2001/040279 | 6/2001 |
| WO | WO/2001/092579 | 12/2001 |
| WO | WO/2009/061640 | 5/2009 |

OTHER PUBLICATIONS

Solmone et al. Journal of Virology 2009; 83: 1718-1726. (Year: 2009).*
Ogata et al. Journal of Medical Virology 1999; 59: 270-276. (Year: 1999).*
Stuyver et al. Hepatology 2001; 33: 751-757. (Year: 2001).*
Yuen et al. Antiviral Research 2007; 75: 64-74. (Year: 2007).*
Margeridon-Thermet et al. The Journal of Infectious Diseases 2009; 199: 1275-1285 (Year: 2009).*
BigDye® Terminator v3.1 Cycle Sequencing Kit Protocol from Applied Biosystems (2010). (Year: 2010).*
Dieffenbach et al. PCR Methods and Applications 1993; 3: S30-S37. (Year: 1993).*
GenBank Accession No. E00010.1 for DNA of Hepatitis B virus (HBV), Nov. 4, 2005, [online], [retrieved on Jul. 20, 2018], retrieved from the Internet, URL: <www.ncbi.nlm.nih.gov/nuccore/e00010>. (Year: 2005).*
GenBank Accession No. Y07587.1 for Hepatitis B virus, complete genome, Mar. 20, 2001, [online], [retrieved on Jul. 20, 2018], retreived from the Internet, URL: <www.ncbi.nlm.nih.gov/nuccore/y07587>. (Year: 2001).*
Vollmer et al. Journal of Clinical Microbiology 2008; 46: 1919-1926 (Year: 2008).*
Lowe et al. Nucleic Acids Research 1990; 18: 1757-1761 (Year: 1990).*
Torresi, J. Journal of Clinical Virology 2002; 25: 97-106 (Year: 2002).*
U.S. Notice of Allowance dated Feb. 2, 2015 issued in U.S. Appl. No. 13/774,960.

(Continued)

*Primary Examiner* — Angela M. Bertagna
(74) *Attorney, Agent, or Firm* — Emily M. Haliday; Weaver Austin Villeneuve & Sampson LLP

(57) ABSTRACT

The present invention provides methods, kits, and oligonucleotides for detecting and analyzing the nucleotide sequence of a reverse transcriptase (RT) region of the polymerase (Pol) gene of Hepatitis B Virus (HBV). In certain embodiments, a target RT region is amplified and subjected to DNA sequencing. The sequence obtained is compared to one or more DNA sequences characteristic of an HBV genotype or serotype, and/or one or more DNA sequences characteristic of an HBV mutation that confers resistance to a drug or vaccine, to determine the HBV genotype or serotype of the amplified product and/or the presence or absence of one or more DNA sequences characteristic of an HBV mutation that confers resistance to a drug or vaccine.

10 Claims, 2 Drawing Sheets

Specification includes a Sequence Listing.

(56) References Cited

OTHER PUBLICATIONS

Abbott Molecular Design Description Overview, "HBV RUO Sequencing", List 03N03-95 and 03N03-85, MD13686 v1, Dec. 2008, 25 pages.
Abbott Molecular Design Description Overview, "HBV Sequencing (CE)", List 03N03-90 and 03N03-80, MD14293_v2, Mar. 2011, 26 pages.
Abramson et al. (1993) "Nucleic acid amplification technologies" *Current Opinion in Biotechnology* 4 (1): 41-47.
Anderson, et al. (1985) "Quantitative Filter Hybridisation", Chapter 4 and "Hybridisation Strategy" Chapter 1, in *Nucleic Acid Hybridisation, IRL Press Limited*, 60 pages.
Barany (1991) "Genetic Disease Detection and DNA Amplification using Cloned Thermostable Ligase" *Proceedings of the National Academy of Sciences USA* 88(1): 189-193.
Barany et al. (1991) "Cloning, Overexpression and Nucleotide Sequence of a Thermostable DNA Ligase-Encoding Gene" *Gene* 109(1): 1-11.
Beaucage et al. (1981) "Deoxynucleoside Phosphoramidites—A New Class of Key Intermediates for Deoxypolynucleotide Synthesis" *Tetrahedron Letters* 22(20): 1859-1862.
Berger et al. (1987) "Guides to Molecular Cloning Techniques" *in Methods in Enzymology* vol. 152, *Academic Press Inc.*, Table of Contents, 8 Pages.
Bi et al. (1997) "CCR: A Rapid and Simple Approach for Mutation Detection" *Nucleic Acids Research* 25(14): 2949-2951.
Boom et al. (1991) "Rapid purification of hepatitis B virus DNA from serum." *J Clin Microbiol* 29(9):1804-11.
Brown et al. (1979) "Chemical Synthesis and Cloning of a Tyrosine tRNA Gene" *Methods in Enzymology* 68: 109-151.
ChangBioscience, 2002, retrieved on [Nov. 7, 2013] Retrieved from the Internet : <URL:http://www.changbioscience.com/protocols/>, Table of Contents, 6 Pages.
Cook (2003) "The Use of NASBA for the Detection of Microbial Pathogens in Food and Environmental Samples" *Journal of Microbiological Methods* 53(2):165-174.
Day et al. (1995) "Detection of Steroid 21-Hydroxylase Alleles Using Gene-Specific PCR and a Multiplexed Ligation Detection Reaction" *Genomics* 29(1):152-162.
Dean et al. (2002) "Comprehensive Human Genome Amplification Using Multiple Displacement Amplification" *Proceedings of the National Academy of Sciences* 99(8):5261-5266.
Demidov (2002) "Rolling-Circle Amplification in DNA Diagnostics: The Power of Simplicity" *Expert Review of Molecular Diagnostics* 2(6):542-548.
Dieffenbach, et al. (1995) "PCR Primer, A Laboratory Manual", *Cold Spring Harbor Laboratory Press*, Table of Contents, 6 pages.
Erlich et al. (1991) "Recent Advances in the Polymerase Chain Reaction" *Science* 252:1643-1651.
Fang et al. (2011) "A complex hepatitis B virus (X/C) recombinant is common in Long an county, Guangxi and may have originated in southern China." *Journal of General Virology* 92(Pt 2): 402-411.
Favis et al. (2000) "Universal DNA Array Detection of Small Insertions and Deletions in BRCA1 and BRCA2" *Nature Biotechnology* 18(5): 561-564.
Heid et al. (1996) "Real Time Quantitative PCR" *Genome Research* 6(10):986-994.
Hsuih et al. (1996) "Novel, Ligation-Dependent PCR Assay for Detection of Hepatitis C Virus in Serum" *Journal of Clinical Microbiology* 34(3):501-507.
Innis et al. (1990) "PCR Protocols—A Guide to Methods and Applications" *Academic Press Inc.*, Table of Contents, 8 Pages.
Lage et al. (2003) "Whole Genome Analysis of Genetic Alterations in Small DNA Samples Using Hyperbranched Strand Displacement Amplification and Array-CGH" *Genome Research* 13(2): 294-307.
Lai et al. (2003) "Viral hepatitis B" *The Lancet* 362(9401): 2089-2094.
Landegren et al. (1988) "A Ligase-mediated Gene Detection Technique," *Science*, 241(4869): 1077-1080.
Leckie et al. (May 8-11, 2011"Development and performance evaluation of the Abbott HBV Sequencing assay for drug resistance, T68" $27^{th}$ *Clinical Virology Symposium Daytona Beach Florida* [Abstract], One Page.
Murray (1989) "Improved double-stranded DNA sequencing using the linear polymerase chain reaction." *Nucleic Acids Res* 17(21): 8889.
Narang et al. (1979) "Improved Phosphotriester Method for the Synthesis of Gene Fragments," *Methods in Enzymology* 68: 90-98.
Norder et al. (1994) "Complete genomes, phylogenic relatedness and structural proteins of six strains of the hepatitis B virus, four of which represent two new genotypes." *Virology* 198(2): 489-503.
Polstra et al. (2002) "Development of Real-Time NASBA Assays with Molecular Beacon Detection to Quantify mRNA Coding for HHV-8 Lytic and Latent Genes," *BMC Infectious Diseases* 2: 18 (10 Pages); http://www.biomedcentral.com/1471-2334/2/18.
Promega, retrieved on [Nov. 4, 2013], Retrieved from the Internet:< URL: http://web.archive.org/web/20040525090258/http://www.promega.com/geneticidproc/ussymp/6procbelgrad3.gif.pdf>, One Page.
Rabenau et al. (2000) "Low Correlation of Serology with Detection of Chlamydia Trachomatis by Ligase Chain Reaction and Antigen EIA," *Infection* 28(2): 97-102.
Rapley (2000) *The Nucleic Acid Protocols Handbook*, Humana Press Table of Contents, 10 Pages.
Ray (2011) "Hepatitis: Genetic variability in HBV resistance." *Nature Reviews Gastroenterology and Hepatology* 8(10): 535.
Read (2001) "Recovery efficiencies of nucleic acid extraction kits as measured by quantitative LightCycler PCR." *J Clin Pathol: Mol Pathol* 54:86-90.
Rozen et al. (2000) "Primer3 on the WWW for General users and for Biologist Programmers," *Methods in Molecular Biology* 132: 365-386.
Saldanha et al. "An International Collaborative Study to Establish a WHO International Standard for HBV DNA Nucleic Acid Amplification Technology Assay." *WHO Expert Committee on Biological Standardization: Fiftieth Report, Geneva, Switzerland*; 1999. *WHO Technical Report Series* No. 904;BS/99.1917.
Sambrook et al. (1989) "Molecular Cloning," *A Laboratory Manual, Second Edition, Cold Spring Harbor Laboratory Press*, Table of Contents, 29 Pages.
Schaefer (2007) "Hepatitis B virus taxonomy and hepatitis B virus genotypes." *World Journal of Gastroenterology* 13(1): 14-21.
Schweitzer et al. (2001) "Combining Nucleic Acid Amplification and Detection," *Current Opinion in Biotechnology* 12(1): 21-27.
Shibayama et al. (2005) "Characterization of seven genotypes (A to E, G and H) of hepatitis B virus recovered from Japanese patients infected with human immunodeficiency virus type 1." *Journal of Medical Virology* 76(1): 24-32.
Valsamakis (2007) "Molecular testing in the diagnosis and management of chronic hepatitis B." *Clinical Microbiological Reviews* 20(3): 426-439.
Walker et al. (1992) "Strand Displacement Amplification—An Isothermal, in Vitro DNA Amplification Technique," *Nucleic Acids Research* 20(7): 1691-1696.
Wang et al. (May 8-11, 2011) "Development and evaluation of HBV_SEQV2 project template for Abbott HBV Sequencing assay, T67" $27^{th}$ *Clinical Virology Symposium Daytona Beach Florida* [Abstract], One Page.
Zirvi et al. (1999) "Ligase-Based Detection of Mononucleotide Repeat Sequences," *Nucleic Acids Research* 27(24): e40 (8 Pages).
Zoulim (2006) "Antiviral therapy of chronic hepatitis B." *Antiviral Research* 71(2-3): 206-215.

\* cited by examiner

Polymerase/RT Mutations from RT53 to RT256
Surface Antigen Mutations from s75 to s225

*Fig. 1*

SEQUENCE LISTING

```
<160> NUMBER OF SEQ ID NOS: 5

<210> SEQ ID NO 1
<211> LENGTH: 25
<212> TYPE: DNA
<213> ORGANISM: Artificial
<220> FEATURE:
<223> OTHER INFORMATION: Primer

<400> SEQUENCE: 1
taggacccct gctcgtgtta caggc                                              25

<210> SEQ ID NO 2
<211> LENGTH: 25
<212> TYPE: DNA
<213> ORGANISM: Artificial
<220> FEATURE:
<223> OTHER INFORMATION: Primer

<400> SEQUENCE: 2 gtggggttg cgtcagcaaa cactt                                               25

<210> SEQ ID NO 3
<211> LENGTH: 31
<212> TYPE: DNA
<213> ORGANISM: Artificial
<220> FEATURE:
<223> OTHER INFORMATION: Primer

<400> SEQUENCE: 3
tatgcctcat cttcttgttg gttcttctgg a                                       31

<210> SEQ ID NO 4
<211> LENGTH: 32
<212> TYPE: DNA
<213> ORGANISM: Artificial
<220> FEATURE:
<223> OTHER INFORMATION: Primer

<400> SEQUENCE: 4
cgaaccactg aacaaatggc actagtaaac tg                                      32

<210> SEQ ID NO 5
<211> LENGTH: 23
<212> TYPE: DNA
<213> ORGANISM: Artificial
<220> FEATURE:
<223> OTHER INFORMATION: Probe

<400> SEQUENCE: 5
agactcgtgg tggacttctc tca                                                23
```

HEPATITIS B VIRUS TYPING AND RESISTANCE ASSAY

CROSS-REFERENCE TO RELATED APPLICATIONS

This application is a continuation of U.S. application Ser. No. 13/774,960, filed Feb. 22, 2013, now U.S. Pat. No. 9,045,803, which claims the benefit of U.S. provisional application No. 61/605,029, filed Feb. 29, 2012, both of which are hereby incorporated by reference in their entireties.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates generally to the area of Hepatitis B Virus (HBV) detection and characterization. In particular, the invention relates to methods and compositions for determining HBV genotype/serotype and for detecting mutations associated with drug resistance and/or vaccine escape.

BACKGROUND OF THE INVENTION

More than 400 million people are chronically infected with HBV, a small, circular, partially double-stranded DNA virus of approximately 3200 base pairs. Chronic infection can result in cirrhosis (scarring) of the liver, liver cancer, liver failure, and death. Current treatment options for chronically infected HBV patients include interferon, peginterferon, and antiviral drugs, such as lamivudine, adefovir, entecavir, telbivudine, and tenofovir targeted against the polymerase (Pol) region of HBV.

The genome of HBV is made of circular DNA, but it is unusual because the DNA is not fully double-stranded. One end of the full-length strand is linked to the viral DNA polymerase. The genome is 3020-3320 nucleotides long (for the full-length strand) and 1700-2800 nucleotides long (for the short length-strand). The negative-sense, (non-coding), is complementary to the viral mRNA. The viral DNA is found in the nucleus soon after infection of the cell. The partially double-stranded DNA is rendered fully double-stranded by completion of the (+) sense strand and removal of a protein molecule from the (−) sense strand and a short sequence of RNA from the (+) sense strand. Non-coding bases are removed from the ends of the (−) sense strand and the ends are rejoined. There are four known genes encoded by the genome, called C, X, P, and S. The core protein is coded for by gene C (HBcAg), and its start codon is preceded by an upstream in-frame AUG start codon from which the pre-core protein is produced. HBeAg is produced by proteolytic processing of the pre-core protein. The DNA polymerase is encoded by gene P (Pol). Gene S is the gene that codes for the surface antigen (HBsAg). The HBsAg gene is one long open reading frame but contains three in frame start (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced. Because of the small size of the genome, many of the open reading frames overlap. For example the S open reading frame overlaps with the Pol open reading frame, specifically, HBV nucleotide positions 155 to 832, coding 226 amino acids of the surface antigen, overlaps with the RT region, nucleotide positions 130 to 1161, of the Pol gene. Drug resistance is associate with mutations in the RT region.

The virus is divided into four major serotypes (adr, adw, ayr, ayw) based on antigenic epitopes presented on its envelope proteins, and into nine genotypes (A-I) according to overall nucleotide sequence variation of the genome. The genotypes have a distinct geographical distribution and are used in tracing the evolution and transmission of the virus. Differences between genotypes affect the disease severity, course and likelihood of complications, and response to treatment and vaccination. Genotypes differ by at least 8% of their sequence and were first reported in 1988 when six were initially described (A-F). Norder H, Courouce A M, Magnius L O (1994). "Complete genomes, phylogenic relatedness and structural proteins of six strains of the hepatitis B virus, four of which represent two new genotypes." Virology 198 (2): 489-503 (incorporated herein by reference for the description of HBV genotypes). Three further types have since been described (G, H, and I). Shibayama T, Masuda G, Ajisawa A, Hiruma K, Tsuda F, Nishizawa T, Takahashi M, Okamoto H (May 2005). "Characterization of seven genotypes (A to E, G and H) of hepatitis B virus recovered from Japanese patients infected with human immunodeficiency virus type 1." Journal of Medical Virology 76 (1): 24-32 (incorporated herein by reference for the description of HBV genotypes). "A complex hepatitis B virus (X/C) recombinant is common in Long An county, Guangxi and may have originated in southern China." Journal of General Virology (2011), 92, 402-411 Journal of General Virology (2011), 92, 402-411. Most genotypes are now divided into subgenotypes with distinct properties. Schaefer S (January 2007). "Hepatitis B virus taxonomy and hepatitis B virus genotypes." World Journal of Gastroenterology: WJG 13 (1): 14-21 (incorporated herein by reference for the description of HBV genotypes).

HBV has a high degree of genetic variation with nine known genotypes (A-I). Different mutations in the various HBV genotypes are associated with how the virus can escape the immune system or become resistant to antiviral drugs. Ray, K, "Hepatitis: Genetic variability in HBV resistance." Nature Reviews Gastroenterology and Hepatology 8, 535 (October 2011) (incorporated herein by reference for the description of HBV mutations associated with immune system/vaccine escape and drug resistance).

SUMMARY OF THE INVENTION

In certain embodiments, the invention provides a method for detecting and analyzing the nucleotide sequence of a reverse transcriptase (RT) region of the polymerase (Pol) gene of Hepatitis B Virus (HBV). The method entails:
  contacting a nucleic acid sample with a primer pair specific for a target RT region and carrying out a real-time amplification reaction to produce and quantify an amplified product if the target RT region is present in the sample;
  determining the DNA sequence of the amplified product; and
  comparing the DNA sequence of the amplified product to:
    one or more DNA sequences characteristic of an HBV genotype or serotype; and/or
    one or more DNA sequences characteristic of an HBV mutation that confers resistance to a drug or vaccine;

to determine the HBV genotype or serotype of the amplified product and/or the presence or absence of one or more DNA sequences characteristic of an HBV mutation that confers resistance to a drug or vaccine. In particular embodiments, the amplified product includes a nucleotide sequence that encodes an amino acid sequence including RT53 through RT256, as numbered from the N-terminus of the RT domain.

In certain embodiments, the DNA sequence of the amplified product is determined using:
a first forward primer that anneals to the HBV genome 5' of nucleotide 286;
a first reverse primer that anneals to the HBV genome 3' of nucleotide 895;
a second forward primer that anneals to the HBV genome between nucleotide 377 and nucleotide 827; and
a second reverse primer that anneals to the HBV genome between nucleotide 377 and nucleotide 827. In various embodiments, the primer pair specific for a target RT region includes: the first forward primer and the first reverse primer; the first forward primer and the second reverse primer; the second forward primer and the first reverse primer; or the second forward primer and the second reverse primer.

The method can additionally include determining amount of amplified product produced and diluting the amplified product by 1:2 to 1:8 prior to DNA sequencing. In various embodiments, the degree of dilution is 1:2, 1:3, 1:4, 1:5, 1:6, 1:7, 1:8 or falls within a range bounded by any of these values. In certain embodiments, the method included diluting the amplified product by either 1:2 or 1:5 prior to sequencing. In particular embodiments, the amplification reaction is a real-time amplification method that is employed to determine the amount of amplified product produced.

In certain embodiments, the amplified product includes at least 270 nucleotides. In particular embodiments, the amplified product includes fewer than 1200 nucleotides, e.g., the amplified product can include between 1000 and 1050 nucleotides.

In various embodiments, the method employs one or more of: a primer that anneals to the HBV genome between nucleotide 180 and nucleotide 204; a primer that anneals to the HBV genome between nucleotide 1178 and nucleotide 1202; a primer that anneals to the HBV genome between nucleotide 420 and nucleotide 450; and/or a primer that anneals to the HBV genome between nucleotide 673 and nucleotide 704. Any of the above-described primers can be at least 24 nucleotides in length. In various embodiments, the method employs one or more of: a primer that has a nucleotide sequence including SEQ ID NO:1; a primer that has a nucleotide sequence including SEQ ID NO:2; a primer that has a nucleotide sequence including SEQ ID NO:3; a primer that has a nucleotide sequence including SEQ ID NO:4.

In illustrative embodiments, at least two primers are employed, and the two primers have nucleotide sequences including: SEQ ID NO:1 and SEQ ID NO:2; SEQ ID NO:1 and SEQ ID NO:3; SEQ ID NO:1 and SEQ ID NO:4; SEQ ID NO:2 and SEQ ID NO:3; SEQ ID NO:2 and SEQ ID NO:4; or SEQ ID NO:3 and SEQ ID NO:4.

In further illustrative embodiments, at least three primers are employed, and the three primers have nucleotide sequences including: SEQ ID NO:1, SEQ ID NO:2, and SEQ ID NO:3; SEQ ID NO:2, SEQ ID NO:3, and SEQ ID NO:4; SEQ ID NO:1, SEQ ID NO:3 and SEQ ID NO:4; SEQ ID NO:1, SEQ ID NO:2, and SEQ ID NO:4; or SEQ ID NO:1, SEQ ID NO:2, SEQ ID NO:3, and SEQ ID NO:4.

In a specific embodiment, at least four primers are employed, and the four primers have nucleotide sequences including SEQ ID NO:1, SEQ ID NO:2, SEQ ID NO:3, and SEQ ID NO:4.

In certain embodiments of the method, a probe is employed to determine the amount of amplified product produced for a sequencing assay. The probe can be, e.g., at least 22 nucleotides in length. In an illustrative embodiment, the probe has a nucleotide sequence including SEQ ID NO:5. In particular embodiments, the probe includes a fluorophore and a quencher at either end of the molecule.

In certain embodiments, the amplification reaction includes polymerase chain reaction (PCR), e.g., real-time polymerase chain reaction (RT-PCR). In particular embodiments, the DNA sequence is determined by cycle DNA sequencing.

In certain embodiments, the nucleic acid sample is obtained from a human patient. In this case, the method can additionally entail recording the HBV genotype or serotype and/or any HBV mutation and/or HBV vaccine escape in a patient medical record, e.g., recording the HBV genotype or serotype and/or any HBV mutation and/or HBV vaccine escape in a computer-readable medium. In various embodiments, the patient medical record is maintained by a laboratory, physician's office, a hospital, a health maintenance organization, an insurance company, or a personal medical record website. In various embodiments, the one or more DNA sequences characteristic of an HBV mutation that confers resistance to a drug include sequences characteristic of HBV mutations that confer resistance to lamivudine, adefovir, entecavir, telbivudine, tenofovir, or any combination thereof. In particular embodiments, the method can additionally include prescribing, initiating, and/or altering therapy for HBV or initiating and/or altering an HBV vaccine therapy. For example, when an HBV mutation that confers resistance to a drug is found to be present in a sample from a patient, the method can include prescribing and/or administering a different drug to the patient. Likewise, when an HBV mutation associated with vaccine escape is found to be present in a sample from a patient, the method can include determining that the patient is not a candidate for treatment with that vaccine.

In particular embodiments, the method has one or more of the following performance characteristics:

The method produces a sequencing result in 95% or more of specimens containing HBV DNA at a concentration of at least 200-400 IU/mL, e.g., at least 200 or at least 400 IU/mL, HBV DNA.

The method has an analytical specificity of 99.5% or greater, e.g., 100.0%, calculated using the frequency of repeatedly reactive results.

The method is capable of detecting mixed bases more than 50% of the time, when the two populations of bases are at equal concentration, for the mixture panel at the $1 \times 10^5$ IU/mL viral load level.

Another aspect of the invention is a kit for detecting and analyzing the nucleotide sequence of a reverse transcriptase (RT) region of the polymerase (Pol) gene of Hepatitis B Virus (HBV). In certain embodiments, the kit includes:
a primer that anneals to the HBV genome 5' of nucleotide 286;
a primer that anneals to the HBV genome 3' of nucleotide 895; and
two primers that anneal to the HBV genome between nucleotide 377 and nucleotide 827.

In particular embodiments, each of the primers is provided in a separate container, and the kit further includes an additional container including a primer pair specific for a target RT region.

In certain embodiments, two of the primers define a target RT region that includes at least 270 nucleotides. In particular embodiments, the target RT region includes fewer than 1200 nucleotides, e.g., the target RT region can include between 1000 and 1050 nucleotides.

In various embodiments, the kit includes one or more of: a primer that anneals to the HBV genome between nucleotide 180 and nucleotide 204; a primer that anneals to the HBV genome between nucleotide 1178 and nucleotide 1202; a primer that anneals to the HBV genome between nucleotide 420 and nucleotide 450; and/or a primer that anneals to the HBV genome between nucleotide 673 and nucleotide 704. Any of the above-described primers can be at least 24 nucleotides in length. In various embodiments, the kit includes one or more of: a primer that has a nucleotide sequence including SEQ ID NO:1; a primer that has a nucleotide sequence including SEQ ID NO:2; a primer that has a nucleotide sequence including SEQ ID NO:3; a primer that has a nucleotide sequence including SEQ ID NO:4.

In illustrative embodiments, the kit includes at least two primers, and the two primers have nucleotide sequences including: SEQ ID NO:1 and SEQ ID NO:2; SEQ ID NO:1 and SEQ ID NO:3; SEQ ID NO:1 and SEQ ID NO:4; SEQ ID NO:2 and SEQ ID NO:3; SEQ ID NO:2 and SEQ ID NO:4; or SEQ ID NO:3 and SEQ ID NO:4.

In further illustrative embodiments, the kit includes at least three primers, and the three primers have nucleotide sequences including: SEQ ID NO:1, SEQ ID NO:2, and SEQ ID NO:3; SEQ ID NO:2, SEQ ID NO:3, and SEQ ID NO:4; SEQ ID NO:1, SEQ ID NO:3 and SEQ ID NO:4; SEQ ID NO:1, SEQ ID NO:2, and SEQ ID NO:4; or SEQ ID NO:1, SEQ ID NO:2, SEQ ID NO:3, and SEQ ID NO:4.

In a specific embodiment, the kit includes at least four primers, and the four primers have nucleotide sequences including SEQ ID NO:1, SEQ ID NO:2, SEQ ID NO:3, and SEQ ID NO:4.

In certain embodiments of the method, the kit includes a probe that anneals to the target RT region. For example, the probe can be present in the additional container including the primer pair specific for a target RT region. The probe can be, e.g., at least 22 nucleotides in length. In an illustrative embodiment, the probe has a nucleotide sequence including SEQ ID NO:5. In particular embodiments, the probe includes a fluorophore and a quencher at either end of the molecule.

Another aspect of the invention is oligonucleotides useful, e.g., as primers and/or probes in the methods described herein. In various embodiments, an oligonucleotide of the invention has a nucleotide sequence consisting of: SEQ ID NO:1; SEQ ID NO:2; SEQ ID NO:3; SEQ ID NO:4; or SEQ ID NO:5.

BRIEF DESCRIPTION OF THE DRAWINGS

FIG. 1: HBV genome and positions of primers. "FP"=forward primer; "RP"=reverse primer; "nt" followed by a number refers to the nucleotide number, numbered from the 5' end of the full-length strand of the HBV genome; "RT" followed by a number refers to the amino acid number, numbered from the N-terminus of the RT domain in the HBV polymerase protein; "s" followed by a number refers to the amino acid number, numbered from the N-terminus of the HBV surface antigen protein (i.e., the "small" or "S" protein).

DETAILED DESCRIPTION

Figure 2:
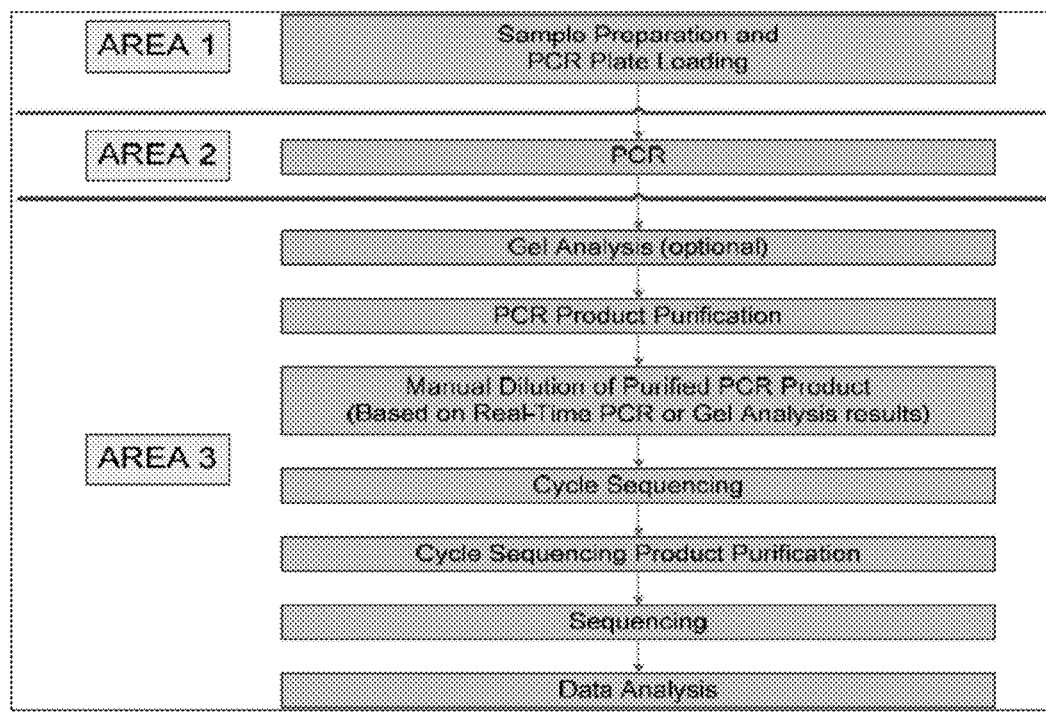
FIG. 2: Schematic of Example 1's HBV Sequencing Assay workflow.

In certain embodiments, the present invention provides oligonucleotide primers and a fluorescently-labeled probe, as well as a novel method for determining the DNA sequence of the reverse transcriptase (RT) region of the polymerase (Pol) gene of Hepatitis B Virus (HBV). In this assay, the nucleotide sequence of the HBV isolate is analyzed for two purposes: to determine the genotype of HBV and to determine if mutations associated with drug resistance are present in the isolate. Both types of information are useful in the management of patients with chronic HBV.

Definitions

Terms used in the claims and specification are defined as set forth below unless otherwise specified.

The term "nucleic acid" refers to a nucleotide polymer, and unless otherwise limited, includes known analogs of natural nucleotides that can function in a similar manner (e.g., hybridize) to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acids, as well as single-stranded molecules. In double- or triple-stranded nucleic acids, the nucleic acid strands need not be coextensive (i.e, a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S.

Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

The term "target nucleic acids" is used herein to refer to particular nucleic acids to be detected in the methods of the invention.

As used herein the term "target nucleotide sequence" refers to a molecule that includes the nucleotide sequence of a target nucleic acid, such as, for example, the amplification product obtained by amplifying a target nucleic acid or the cDNA produced upon reverse transcription of an RNA target nucleic acid.

As used herein, the term "complementary" refers to the capacity for precise pairing between two nucleotides. I.e., if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In particular embodiments, hybridizations are carried out under stringent hybridization conditions. The phrase "stringent hybridization conditions" generally refers to a temperature in a range from about 5° C. to about 20° C. or 25° C. below than the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the $T_m$ value may be calculated by the equation: $T_m=81.5+0.41(\% \text{ G+C})$, when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Illustrative stringent conditions suitable for achieving specific hybridization of most sequences are: a temperature of at least about 60° C. and a salt concentration of about 0.2 molar at pH7.

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

A "probe" is a nucleic acid capable of binding to a target nucleic acid of complementary sequence through one or more types of chemical bonds, generally through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-30 nucleotides in length).

The primer or probe can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

"Amplification" encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

The term "qPCR" is used herein to refer to quantitative real-time polymerase chain reaction (PCR), which is also known as "real-time PCR" or "kinetic polymerase chain reaction."

A "reagent" refers broadly to any agent used in a reaction, other than the analyte (e.g., nucleic acid being analyzed). Illustrative reagents for a nucleic acid amplification reaction include, but are not limited to, buffer, metal ions, polymerase, reverse transcriptase, primers, template nucleic acid, nucleotides, labels, dyes, nucleases, and the like. Reagents for enzyme reactions include, for example, substrates, cofactors, buffer, metal ions, inhibitors, and activators.

"Hydrolysis probes" are generally described in U.S. Pat. No. 5,210,015, which is incorporated herein by reference in its entirety for its description of hydrolysis probes. Hydrolysis probes take advantage of the 5'-nuclease activity present in the thermostable Taq polymerase enzyme typically used in the PCR reaction (TagMan® probe technology, Applied Biosystems, Foster City Calif.). The hydrolysis probe is labeled with a fluorescent detector dye such as fluorescin, and an acceptor dye or quencher. In general, the fluorescent dye is covalently attached to the 5' end of the probe and the quencher is attached to the 3' end of the probe, and when the probe is intact, the fluorescence of the detector dye is quenched by fluorescence resonance energy transfer (FRET). The probe anneals downstream of one of the primers that defines one end of the target nucleic acid in a PCR reaction. Using the polymerase activity of the Taq enzyme, amplification of the target nucleic acid is directed by one primer that is upstream of the probe and a second primer that is downstream of the probe but anneals to the opposite strand of the target nucleic acid. As the upstream primer is extended, the Taq polymerase reaches the region where the labeled probe is annealed, recognizes the probe-template hybrid as a substrate, and hydrolyzes phosphodiester bonds of the probe. The hydrolysis reaction irrevocably releases the quenching effect of the quencher dye on the reporter dye, thus resulting in increasing detector fluorescence with each successive PCR cycle. In particular, hydrolysis probes suitable for use in the invention can be capable of detecting 8-mer or 9-mer motifs that are common in the human and other genomes and/or transcriptomes and can have a high $T_m$ of about 70° C. enabled by the use of linked nucleic acid (LNA) analogs.

The term "label," as used herein, refers to any atom or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "dye," as used herein, generally refers to any organic or inorganic molecule that absorbs electromagnetic radiation at a wavelength greater than or equal 340 nm.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The "reverse transcriptase (RT) region of the polymerase (Pol) gene of Hepatitis B Virus (HBV)" is a region of the HBV Pol gene that encodes the RT domain. More specifically, the HBV polymerase protein can be divided into 4 domains (terminal protein, spacer, RT, ribonuclease H), and each of these can be numbered separately. As used herein, the HBV RT domain starts with the highly conserved EDWGPCDEHG motif, contains 344 amino acids, and, as an example of resistance against anti-HBV drug therapies, the lamivudine-related resistance mutations are found at amino acid rtL180M and rtM204V/I (previously 552, 550, 539, or 549).

As used herein, the "target RT region" is a region of the HBV Pol gene that overlaps with the surface antigen (SA) gene.

HBV nucleotide numbers are numbered from nucleotide 1 of the circular genome, which, by convention begins at an EcoRI cleavage site.

Amplification and DNA Sequencing for HBV Typing and Resistance Determination—In General In particular embodiments, the invention includes an amplification and DNA sequencing method for detecting and analyzing the nucleotide sequence of a reverse transcriptase (RT) region of the polymerase (Pol) gene of Hepatitis B Virus (HBV). The method is carried out to determine the HBV genotype or serotype of a product amplified from this region and/or the presence or absence of one or more DNA sequences characteristic of an HBV mutation that confers resistance to a drug or vaccine. In preferred embodiments, both types of information are derived from one amplification and sequencing assay. The method entails contacting a nucleic acid sample with a primer pair specific for a target RT region and carrying out an amplification reaction to produce and quantify an amplified product if the target RT region is present in the sample. If an amplified product is obtained, its DNA sequence is then determined and compared to one or more DNA sequences characteristic of an HBV genotype or serotype; and/or one or more DNA sequences characteristic of an HBV mutation that confers resistance to a drug or vaccine. The DNA sequences characteristic of the nine major HBV genotypes (A-I) and four major serotypes (adr, adw, ayr, ayw) are well known (see Background section). The DNA sequence comparison can also be carried out to determine HBV subgenotype, as well as HBV genotype and/or serotype, including any genotype, subgenotype, or serotype for which DNA sequence information becomes available in the future. DNA sequences characteristic of mutations that confer resistance to a drug or vaccine are also well known (see Background section). In various embodiments, such mutations include those that confer resistance to lamivudine, adefovir, entecavir, telbivudine, tenofovir, or any combination thereof. Furthermore, the DNA sequence comparison can be carried out with DNA sequences that are identified in the future as conferring resistance to any available HBV drug or vaccine.

Amplification can be carried out using any suitable amplification method, such as, e.g., polymerase chain reaction (PCR). In particular embodiments, the amplification reaction is a real-time amplification reaction, such as real-time PCR (RT-PCT). Amplification methods are described in greater detail below. DNA sequencing can also be carried out using any of the various available DNA sequencing methods, such as, e.g., cycle DNA sequencing. DNA sequencing methods are described in more detail below.

In certain embodiments, the method additionally includes determining amount of amplified product produced and, optionally, diluting the amplified product prior to sequencing. The amplified product can be readily quantified during real-time amplification by any of a variety of available methods. If the concentration of the amplified product is appropriate for the selected DNA sequencing method, the amplified product can be sequenced without adjusting its concentration. However, if the concentration of the amplified product is not appropriate for the selected DNA sequencing method, the amplified product may be concentrated or, more typically, diluted to a more appropriate level. In various embodiments, the degree of dilution is 1:2, 1:3, 1:4, 1:5, 1:6, 1:7, 1:8 or falls within a range bounded by any of these values. In certain embodiments, the method included diluting the amplified product by either 1:2 or 1:5 prior to sequencing. Quantitation of the amplified product thus offers the advantage that conditions can be adjusted to provide better sequencing results than in the absence of quantitation.

The primer pair specific for a target RT region is selected to produce an amplified product that includes one or more sites that vary among genotypes, subgenotypes, and/or serotypes and/or one or more sites associated with drug or vaccine resistance. In various embodiments, this primer pair is selected to produce an amplified product that includes at least about: 250, 300, 350, 400, 450, 500, 550, 600, 650, 700, 750, 800, 850, 900, 950, 1000, 1050, 1100, 1150, 1200, or 1250 nucleotides, or any number of nucleotides falling within any range bounded by any of these values, e.g., 1000-1050. In certain embodiments, this primer pair is selected to produce an amplified product includes a nucleotide sequence that encodes an amino acid sequence including RT53 through RT256, as numbered from the N-terminus of the RT domain. See FIG. 1. Primer design and illustrative primers are described further below.

In particular embodiments, the DNA sequence of the amplified product is determined using primers. The number of primers employed is generally sufficient to obtain DNA sequence for regions of interest. In certain embodiments, 4 primers are employed, namely:
  a primer that anneals to the HBV genome 5' of nucleotide 286, which can be employed as a first forward primer;
  a primer that anneals to the HBV genome 3' of nucleotide 895, which can be employed as a first reverse primer;
  a primer that anneals to the HBV genome between nucleotide 377 and nucleotide 827, which can be employed as a second forward primer; and
  a primer that anneals to the HBV genome between nucleotide 377 and nucleotide 827, which can be employed as a second reverse primer (in this case, this primer will anneal to the HBV genome "downstream" of the second forward primer).

In some embodiments, one or more of the same primers can be used in the primer pair specific for a target RT region and as a DNA sequencing primer(s). In various embodiments, the primer pair specific for a target RT region can include: (1) the first forward primer and the first reverse primer, (2) the first forward primer and the second reverse primer, (3) the second forward primer and the first reverse primer, (4) the second forward primer and the second reverse primer (in each of these instances, the primer designations refer to those introduced above).

The methods described herein can be carried out to analyze nucleic acid samples obtained from human patients, e.g., those known to have, or suspected of having, an HBV infection. The information obtained (e.g., HBV genotype or serotype and/or any HBV mutation associated with drug resistance and/or HBV vaccine escape) can, in certain embodiments, be recorded in a patient medical record, which can entail recording the information in a computer-readable medium. The patient medical record can be one that is maintained by a laboratory, physician's office, a hospital, a health maintenance organization, an insurance company, or on a personal medical record website.

In certain embodiments, the methods described above can additionally include adjusting the treatment of a patient based on the information obtained. Thus, the methods can include prescribing, initiating, and/or altering drug therapy for HBV. For example, if the results indicate the presence of an HBV strain having no known mutations associated with drug or vaccine resistance, a clinician can choose from among all available drug and vaccine treatments. However, if the results indicate the presence of an HBV strain with a drug resistance mutation, the clinician could prescribe, initiate therapy with, or alter therapy to a different drug or a vaccine. Similarly, if the results indicate the presence of an HBV strain with a mutation associated with vaccine escape, the clinician could prescribe initiate therapy with, or alter therapy to anti-HBV immunoglobulin (HBIG), or a drug.

Sample Nucleic Acids

Preparations of nucleic acids ("samples") can be obtained from biological sources and prepared using conventional methods known in the art. In particular, DNA or RNA useful in the methods described herein can be extracted and/or amplified from any source, typically a sample from a human subject, such as a patient known to have, or suspected of having, an HBV infection. Nucleic acids can be extracted or amplified from cells, bodily fluids (e.g., blood, a blood fraction, etc.), or tissue samples by any of a variety of standard techniques. Illustrative samples include samples of plasma, serum, blood cells, stem cells, or tumors.

Nucleic acids of interest can be isolated using methods well known in the art, with the choice of a specific method depending on the source, the nature of nucleic acid, and similar factors. The sample nucleic acids need not be in pure form, but are typically sufficiently pure to allow the amplification and DNA sequencing steps of the methods described herein to be performed.

Primers

Primers suitable for nucleic acid amplification are sufficiently long to prime the synthesis of extension products in the presence of the agent for polymerization. The exact length and composition of the primer will depend on many factors, including, for example, temperature of the annealing reaction, source and composition of the primer, and where a probe is employed, proximity of the probe annealing site to the primer annealing site and ratio of primer:probe concentration. For example, depending on the complexity of the target nucleic acid sequence, an oligonucleotide primer typically contains in the range of about 15 to about 30 nucleotides, although it may contain more or fewer nucleotides. In various embodiments, the primer contains 15, 16, 17, 18, 19, 20, 21, 22, 23, 24, 25, 26, 27, 28, 29, or 30 nucleotides, or a number of nucleotides falling within any range bounded by any of these values. The primers should be sufficiently complementary to selectively anneal to their respective strands and form stable duplexes. One skilled in the art knows how to select appropriate primer pairs to amplify the target nucleic acid of interest.

For example, PCR primers can be designed by using any commercially available software or open source software, such as Primer3 (see, e.g., Rozen and Skaletsky (2000) Meth. Mol. Biol., 132: 365-386; www.broad.mit.edu/node/1060, and the like) or by accessing the Roche UPL website. The amplicon sequences are input into the Primer3 program with the UPL probe sequences in brackets to ensure that the Primer3 program will design primers on either side of the bracketed probe sequence.

Primers may be prepared by any suitable method, including, for example, cloning and restriction of appropriate sequences or direct chemical synthesis by methods such as the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; the solid support method of U.S. Pat. No. 4,458,066 and the like, or can be provided from a commercial source.

Primers may be purified by using a Sephadex column (Amersham Biosciences, Inc., Piscataway, N.J.) or other methods known to those skilled in the art. Primer purification may improve the sensitivity of the methods of the invention.

In certain embodiments, the method described herein are carried out using one or more of the following primers:

(1) A primer that anneals to the HBV genome between nucleotide 180 and nucleotide 204, which can be employed as a first forward primer for DNA sequencing and/or as the forward primer in a primer pair specific for a target RT region, see, e.g., SEQ ID NO:1 in Table 1. This primer anneals to the third nucleotide of the codon for amino acid 17 through the third nucleotide of the codon for amino acid 25 of the RT region, corresponding to the second nucleotide of the codon for amino acid 9 through the second nucleotide of the codon for amino acid 17 of the surface antigen region.

(2) A primer that anneals to the HBV genome between nucleotide 1178 and nucleotide 1202, which can be employed as a first reverse primer for DNA sequencing and/or as the reverse primer in a primer pair specific for a target RT region, see, e.g., SEQ ID NO:2 in Table 1. This primer anneals beyond the last nucleotide of the RT region and the surface antigen region; corresponding to the second nucleotide of the codon for amino acid 6 through the second nucleotide of the codon for amino acid 14 of the RNaseH region of the polymerase gene).

(3) A primer that anneals to the HBV genome between nucleotide 420 and nucleotide 450, which can be employed as a second forward primer for DNA sequencing and/or as the forward primer in a primer pair specific for a target RT region, see, e.g., SEQ ID NO:3 in Table 1. This primer anneals to the third nucleotide of the codon for amino acid 97 through the third nucleotide of the codon for amino acid 107 of the RT region, corresponding to the second nucleotide of the codon for amino acid 89 through the second nucleotide of the codon for amino acid 99 of the surface antigen region.

(4) A primer that anneals to the HBV genome between nucleotide 673 and nucleotide 704, which can be employed as a second reverse primer for DNA sequencing and/or as the reverse primer in a primer pair specific for a target RT region, see, e.g., SEQ ID NO:4 in Table 1. This primer anneals to the first nucleotide of the codon for amino acid 182 through the second nucleotide of the codon for amino acid 192 of the RT region, corresponding to the third nucleotide of the codon for amino acid 173 through the first nucleotide of the codon for amino acid 184 of the surface antigen region).

TABLE 1

| SEQ ID NO. | Nucleotide Sequence |
|---|---|
| SEQ ID NO: 1 | 5' TAGGACCCCTGCTCGTGTTACAGGC 3' |
| SEQ ID NO: 2 | 5' GTGGGGGTTGCGTCAGCAAACACTT 3' |
| SEQ ID NO: 3 | 5' TATGCCTCATCTTCTTGTTGGTTCTTCTGGA 3' |
| SEQ ID NO: 4 | 5' CGAACCACTGAACAAATGGCACTAGTAAACTG 3' |

Primers useful in the methods described herein can comprise (include), consist essentially of, or consist of any of SEQ ID NOs:1-4. A primer that "consists essentially of" a given sequence includes a sufficient portion of that sequence to have the basic and novel characteristic of specifically hybridizing to the complementary sequence under the assay conditions; however, such a primer may lack one or more nucleotides of the given sequence and/or may include additional nucleotides. In various embodiments, a primer that "consists essentially of" a given sequence is at least 60%, 65%, 70%, 75%, 80%, 85% 90%, or 95% identical to that sequence or has a degree of sequence identity that falls within a range bounded by any of these values.

Probe

In certain embodiments, a probe is employed to determine the amount of amplified product produced, e.g., for a sequencing assay. Probes are designed and employed to hybridize selectively to the target nucleic acids of interest. Probes can be perfectly complementary to the target nucleic acid sequence or can be less than perfectly complementary. As those of skill in the art appreciate many of the considerations for designing, making, and purifying primers also apply to designing, making, and purifying probes. In particular, probes are typically in the range of about 15 to about 30 nucleotides, although they may contain more or fewer nucleotides. In various embodiments, the probe contains 15, 16, 17, 18, 19, 20, 21, 22, 23, 24, 25, 26, 27, 28, 29, or 30 nucleotides, or a number of nucleotides falling within any range bounded by any of these values.

Probes useful in the methods described herein can hybridize to any suitable sequence in the amplified product, although preferred probes do not hybridize to primer sequences. In an illustrative embodiment, the probe has a nucleotide sequence including 5' AGACTCGTGGTGGACTTCTCTCA 3'(SEQ ID NO:5), which hybrizes to nucleotides 250-272 of the HBV genome. This probe can be used, e.g., to detect an amplified product produced using any of the following primer pairs:

SEQ ID NO:1 and SEQ ID NO:2;
SEQ ID NO:1 and SEQ ID NO:4;
SEQ ID NO:3 and SEQ ID NO:2; and
SEQ ID NO:3 and SEQ ID NO:4.

In certain embodiments, the probe is labeled. Where quantification of amplified product is carried out in a real-time amplification method, the probe is conveniently labeled with one or more fluorescent label(s). In an illustrative embodiment, the probe includes a fluorophore and a quencher at either end of the molecule, e.g., 5' Quasar 670 AGACTCGTGGTGGACTTCTCTCA-BHQ2 3' (SEQ ID NO:5). Such a probe can be used in a fluorogenic nuclease assay for real-time quantification (see below).

The illustrative probe described herein can comprise (include), consist essentially of, or consist of SEQ ID NO:5. A probe that "consists essentially of" a given sequence includes a sufficient portion of that sequence to have the basic and novel characteristic of specifically hybridizing to the complementary sequence under the assay conditions; however, such a primer may lack one or more nucleotides of the given sequence and/or may include additional nucleotides. In various embodiments, a probe that "consists essentially of" a given sequence is at least 60%, 65%, 70%, 75%, 80%, 85% 90%, or 95% identical to that sequence or has a degree of sequence identity that falls within a range bounded by any of these values.

Amplification Methods

Any method of detection and/or quantification of nucleic acids can be used in the invention to detect amplification products. In one embodiment, PCR (polymerase chain reaction) is used to amplify and/or quantify target nucleic acids. In other embodiments, other amplification systems or detection systems are used, including, e.g., systems described in U.S. Pat. No. 7,118,910 (which is incorporated herein by reference in its entirety for its description of amplification/detection systems) and Invader assays; PE BioSystems). In particular embodiments, real-time quantification methods are used. For example, "quantitative real-time PCR" methods can be used to determine the quantity of a target nucleic acid present in a sample by measuring the amount of amplification product formed during the amplification process itself.

Fluorogenic nuclease assays are one specific example of a real-time quantification method that can be used successfully in the methods described herein. This method of monitoring the formation of amplification product involves the continuous measurement of PCR product accumulation using a dual-labeled fluorogenic oligonucleotide probe—an approach frequently referred to in the literature as the "TaqMan® method." See U.S. Pat. No. 5,723,591; Heid et al., 1996, Real-time quantitative PCR Genome Res. 6:986-94, each incorporated herein by reference in their entireties for their descriptions of fluorogenic nuclease assays. It will be appreciated that while "TaqMan® probes" are the most widely used for quantitative real-time PCR, the invention is not limited to use of these probes; any suitable probe can be used.

Other detection/quantification methods that can be employed in the methods described herein include FRET and template extension reactions, molecular beacon detection, Scorpion detection, Invader detection, and padlock probe detection.

DNA Sequencing Methods

The amplified product obtained from the amplification reaction can be sequenced using any conventional sequencing method, including traditional Sanger sequencing (chain-terminator sequencing), cycle DNA sequencing (dye-terminator sequencing, and high-throughput methods, such as Lynx Therapeutics' Massively Parallel Signature Sequencing (MPSS), Polony sequencing, 454 pyrosequencing, Illumina (Solexa) sequencing, SOLiD sequencing, Ion semiconductor sequencing, DNA nanoball sequencing, Helioscope™ single molecule sequencing, Single Molecule SMRT™ sequencing, Single Molecule real time (RNAP) sequencing, Nanopore DNA sequencing, and VisiGen Biotechnologies sequencing. The amplified product can also be sequenced by hybridization or mass spectroscopy.

In an illustrative embodiment, cycle DNA sequencing is employed to sequence the amplified product. See Example below. "Cycle DNA sequencing" refers to a modification of the traditional Sanger sequencing method in which dideoxynucleotides are used in a polymerization reaction to create a nested set of DNA fragments with dideoxynucleotides at the 3' terminus of each fragment. Cycle sequencing employs a thermostable DNA polymerase that can be heated to a temperature that denatures double-stranded DNA and still retain activity. The sequencing reaction can be repeated over and over again in the same tube by heating the mixture to denature the DNA and then allowing it to cool to anneal the primers and polymerize new strands.

Removal of Undesired Reaction Components

It will be appreciated that reactions involving complex mixtures of nucleic acids in which a number of reactive steps are employed can result in a variety of unincorporated reaction components, and that removal of such unincorporated reaction components, or reduction of their concentration, by any of a variety of clean-up procedures can improve the efficiency and specificity of subsequently occurring reactions. In certain embodiments, the concentration of undesired components can be reduced by simple dilution. In particular embodiments, undesired components can be removed by a variety of enzymatic means. Alternatively, or in addition to the above-described methods, undesired components can be removed by purification.

Assay Performance

The assay methods described above were validated as described in Examples 2-7. Design validation testing was evaluated using two assay formats: A-m2000sp for sample preparation, m2000rt for PCR and PCR product quantitation and determination of dilution factor, ExoSAP-IT for post-PCR clean-up, Perkin Elmer (PE) 9700 for cycle sequencing, sodium acetate/ethanol for post-cycle sequencing clean-up, and Applied Biosystems 3130xl for sequence analysis; B-m24sp for sample preparation, PE 9700 for PCR, agarose gel analysis for PCR product quantitation and determination of dilution factor, Qiagen column for post-PCR clean-up, PE 9700 for cycle sequencing, isopropanol for post-cycle sequencing clean-up, and AB 3130xl for sequence analysis.

Participants were trained using review of the package insert and the Operations Manuals and performed training runs that included run controls and HBV samples. Following training, each participant executed one run: format A or format B. Instrument format A runs contained Negative Control, Positive Control, 23 HBV-negative samples and 23 HBV-positive samples (including some samples near the assay limit of detection). Instrument format B runs contained Negative Control, Positive Control, 8 HBV-negative samples, and 8 HBV-positive samples (including some samples near the assay limit of detection).

The expected results were assigned by the R&D group based on the target types, i.e., a positive sample was expected to provide valid HBV sequence, while a negative sample should have provided a PCR-negative result.

The validation established that the assay methods described above fully meet the need for a reliable HBV sequencing assay for detection of HBV drug resistance mutations and for determination of HBV genotype in plasma or serum, with sensitivity comparable to or better than other equivalent commercially available assays. More specifically, certain embodiments of assay methods were tested and found the meet the following acceptance criteria: The overall agreement rate between valid sample results and the expected results shall be 95.0% or greater. HBV-negative samples should have PCR-negative results, and HBV-positive samples (including some samples near the assay limit of detection) should have PCR-positive results and valid sequence. A valid sequence is defined as one where the sequence is of high quality (>99.0% accurate at the base level, covers the biological region of interest with 3-4 primer sequences per sample, and is HBV because it lines up against the HBV reference sequence). A valid sequence is also sequence that is available for analysis using sequence analysis programs where genotype and presence of mutations associated with drug resistance can be determined. In particular, the test results demonstrated that all negative specimens gave the expected negative results, while all the positive specimens were sequenced with high quality sequence results.

In some embodiments, the assay method produces a sequencing result in 95% or more of specimens containing HBV DNA at a concentration of at least 1200, 1000, 800, 600, 400 or 200 IU/mL HBV DNA, e.g., when 0.5 mL is tested. See Examples 2 and 3. In particular embodiment, the assay method produces a sequencing result in 95% or more of specimens containing HBV DNA at a concentration falling within a range defined by any of these values (e.g., 200-400 IU/mL HBV DNA). In specific embodiments, this criterion is met when a perfect match exists between the primers and probe and the specimen nucleotide sequence.

In certain embodiments, the assay method produces the same result more than 95.0% of the time (where agreement is defined as >98% agreement at the base-pair level in the HBV genome sequence 337-909), when used to test plasma (ACD-A, CPD, sodium EDTA, potassium EDTA), and serum.

In particular embodiments, the assay method produces the same result ≥95.0% of the time (where agreement is defined as ≥98% agreement at the base-pair level in the HBV genome sequence 337-909), when used to test anti-coagulated plasma (ACD-A, CPD, sodium EDTA, potassium EDTA), and serum. For example, certain embodiments of the assay methods described herein were tested as follows: Fifty matched sets (potassium EDTA, sodium EDTA, CPD and ACD-D plasma and serum) were tested; 25 of them were HBV-negative, and 25 of them were HBV positive. As compared to the serum control, 100% (95% CI 98.17%-100%) of the 200 pairs were matched acceptably.

In some embodiments, the assay method is capable of detecting mixed bases greater than 50% of the time, when the two populations of bases are at equal concentration, for the mixture panel at the 1×105 IU/mL viral load level. See Example 4.

In certain embodiments, the assay method produces the same result ≥95.0% of the time (where agreement is defined as ≥98% agreement at the base-pair level in the HBV genome sequence 337-909), when used to test specimens containing potential cross-reactants and interfering substances found in patient samples. See Example 5.

In particular embodiments, the assay method has an analytical specificity of 99.5% or greater, calculated using the frequency of repeatedly reactive (i.e., false positive) results, when used to test specimens from HBV-negative people. In variations of such embodiments, the analytical specificity is 100.0%. See Example 6.

In some embodiments, the assay method provides a total sample preparation, amplification, sequence generation, and sequence analysis time of less than 72 hours per plate (24 results). In variations of such embodiments, the total sample preparation, amplification, sequence generation, and sequence analysis time is less than 30 hours, e.g., about 25 hours.

In certain embodiments, 95.0% or more of completed runs are valid when judged by run controls, e.g., when at least 50 runs are performed. For example, the valid rate for m2000sp/m2000rt runs was tested and found to be 98.1% (52/53). The valid rate for m24sp/PE9700/Agarose Gel runs was tested and found to be 100.0% (16/16).

The embodiment described in detail in Example 1 meets all of the performance criteria described above.

Kits

Kits according to the invention include one or more reagents useful for practicing one or more assay methods of the invention. A kit generally includes a package with one or more containers holding the reagent(s) (e.g., primers and/or probe(s)), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits according to the invention generally include instructions for carrying out one or more of the methods described herein. Instructions included in such kits can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

In certain embodiments, a kit for detecting and analyzing the nucleotide sequence of a reverse transcriptase (RT) region of the polymerase (Pol) gene of Hepatitis B Virus (HBV) includes:

a primer that anneals to the HBV genome 5' of nucleotide 286;

a primer that anneals to the HBV genome 3' of nucleotide 895; and two primers that anneal to the HBV genome between nucleotide 377 and nucleotide 827.

In various embodiments, two of the primers in the kit define a target RT region that includes at least about: 250, 300, 350, 400, 450, 500, 550, 600, 650, 700, 750, 800, 850, 900, 950, 1000, 1050, 1100, 1150, 1200, or 1250 nucleotides, or any number of nucleotides falling within any range bounded by any of these values, e.g., 1000-1050.

In particular embodiments, the kit can include one or more of the following primers:

a primer that anneals to the HBV genome between nucleotide 180 and nucleotide 204, see, e.g., SEQ ID NO:1 in Table 1 (above);

a primer that anneals to the HBV genome between nucleotide 1178 and nucleotide 1202, see, e.g., SEQ ID NO:1 in Table 1 (above);

a primer that anneals to the HBV genome between nucleotide 420 and nucleotide 450, see, e.g., SEQ ID NO:1 in Table 1 (above); and a primer that anneals to the HBV genome between nucleotide 673 and nucleotide 704, see, e.g., SEQ ID NO:1 in Table 1 (above).

The kit can also include a probe described herein, optionally in combination with one or more of the primers described herein. For example, the kit can include an illustrative probe that has a nucleotide sequence including 5' AGACTCGTGGTGGACTTCTCTCA 3' (SEQ ID NO:5).

In certain embodiments, the probe is labeled, e.g., 5' Quasar 670 AGACTCGTGGTGGACTTCTCTCA-BHQ2 3' (SEQ ID NO:5).

The primers and/or probe described herein can be package in any manner that facilitates their use in the methods described above. For example, a container can include a primer pair specific for a target RT region to produce the amplified product, and a primer(s) for DNA sequencing can be provided in a separate container or container(s).

EXAMPLES

Example 1

HBV Sequencing Assay

Biological Principles of the Procedure

The HBV Sequencing assay consists of two kits: the HBV Sequencing Control Kit and the HBV Sequencing Reagent Kit.

The HBV Sequencing assay uses PCR to generate amplified product from the polymerase region of the HBV DNA genome in clinical specimens. The presence of HBV amplification products is detected by measuring the fluorescence of the HBV probe that binds to the target during the extension/anneal step or by agarose gel electrophoresis. The amplified product is purified to remove unused primers and deoxynucleotide triphosphates (dNTPs) using ExoSAP-IT® (United States Biochemical (USB) Corporation) or spin columns (QIAGEN). An optimal quantity of purified amplified product is subjected to Sanger-based cycle sequencing. The cycle sequencing products are purified using sodium acetate/ethanol or isopropanol precipitation and resuspended in formamide prior to electrophoresis on an Applied Biosystems (AB) Genetic Analyzer (3130, 3130xl). DNA sequence data are analyzed using the programs: AB SegScape® and web-based programs, such as Evivar or Genafor. The resulting information can be used to help manage anti-HBV therapy.

Sample Preparation

The purpose of sample preparation is to extract and concentrate target DNA, to make the target accessible for amplification, and to remove potential inhibitors of amplification from the extract. This process is accomplished by the m2000sp, an automated sample preparation system designed to use magnetic microparticle processes for the purification of nucleic acids from samples. The Abbott m Sample Preparation System$_{DNA}$ (4×24 Preps) reagents are used to lyse the virion, capture the nucleic acids and wash the particles to remove unbound sample components. Proteinase K is included in the lysis step to digest proteins associated with the nucleic acids.[4,5] The bound nucleic acids are eluted and transferred to a 96-deep well plate. The nucleic acids are then ready for amplification. Sample preparation may also be performed using the m24sp or manually.

Reagent Preparation and Reaction Plate Assembly

The HBV Sequencing amplification reagent components (HBV Pol PCR Mix, AmpliTaq Gold® Enzyme, Activation Reagent, and Uracil-DNA-Glycosylase (UNG)) are assembled by the operator. The Abbott m2000sp is used to dispense the resulting master mix to the Abbott 96-Well Optical Reaction Plate along with nucleic acid samples prepared by the Abbott m2000sp. The plate is ready, after manual application of the Abbott Optical Adhesive Cover, for transfer to the Abbott m2000rt. Alternatively, the mastermix and samples can be manually dispensed, before amplification in a PE 9700 thermal cycler or equivalent.

Amplification

During the amplification/detection reaction, the target DNA is amplified by AmpliTaq Gold Enzyme in the presence of primers, Quasar-labeled probe, deoxynucleotide triphosphates (dNTPs), deoxyuridine triphosphate (dUTP), UNG and magnesium chloride. First, the HBV primers anneal to their respective targets and are extended by the polymerase. After a denaturation step in which the temperature of the reaction is raised above the melting point of the double-stranded DNA product, the newly created DNA strand is denatured from the target DNA. During each round of thermal cycling, amplification products dissociate to single strands at high temperature allowing primer annealing and extension as the temperature is lowered. Exponential amplification of the product is achieved through repeated cycling between high and lower temperatures, resulting in a billion-fold or greater amplification of target sequences. The target sequence for the HBV Sequencing assay includes a portion of the polymerase and overlapping Surface Antigen gene in the HBV genome. This region is specific for HBV and is highly conserved. The primers are designed to hybridize to this region with the fewest possible mismatches among HBV genotypes A through H.

Detection

The presence of HBV amplification products is detected during the anneal/extension step by measuring the fluorescence of the Quasar-labeled HBV probe that binds to the target during the anneal/extension step. The HBV probe is a single-stranded DNA oligonucleotide consisting of a probe sequence with a fluorescent moiety that is covalently linked to the 5' end of the probe and a quenching moiety that is covalently linked to the 3' end of the probe. In the absence of the HBV target sequence, probe fluorescence is quenched. In the presence of HBV, the HBV probe specifically binds to the target. This separates the fluorophore from the quencher, allowing fluorescent emission and detection. The amplification cycle at which fluorescent signal is detected by the Abbott m2000rt is proportional to the log of the HBV DNA concentration present in the original sample. Alternatively, if an m2000rt was not used for amplification, detection of PCR product may be performed using agarose gel analysis.

PCR Product Purification

The seal is removed from the Abbott 96-Well Optical Reaction Plate, and the PCR reactions are purified to remove unused primers and reaction components that may interfere with subsequent cycle sequencing reactions. Purification is achieved using ExoSAP-IT (USB), a reagent that consists of a mixture of exonuclease I for degradation of single-stranded primers, and Shrimp Alkaline Phosphatase for removal of phosphate from dNTPs thus rendering them non-functional. Purification can also be achieved using a size separation spin column (QIAGEN).

Quantitation and Dilution

Quantitation of amplified product is achieved using the Cycle Number (CN) results from the m2000rt or by gel analysis. If amplicon is detected, it can be diluted 1:2 or 1:5 to ensure that the optimal quantity of amplified product is added to cycle sequencing reactions.

Cycle Sequencing

Pol amplified product of each specimen is analyzed using four different cycle sequencing reactions. Each type of cycle sequencing reactions contains amplified product, a unique primer, and BigDye® Terminator v3.1 (Applied Biosystems). Sequencing mixtures and purified amplified products are manually added to Abbott 96-Well Optical Reaction Plate which is then sealed prior to cycle sequencing. During each thermal cycling step, the primer hybridizes to the amplified product and BigDye Terminator extends the length of the complementary strands. Because a minor proportion of the substrate dNTPs are fluorescently-labeled dideoxynucleotides (ddNTPs), chain termination occurs at each position in a minority of the growing chains. Each base-type of ddNTPs (A, C, G, T) is labeled with a different fluorophore. Chain termination results in the generation of extension product, each one nucleotide longer than its predecessor.[6]

Cycle Sequencing Purification

The seal is removed from the Abbott 96-Well Optical Reaction Plate, and the cycle sequencing reactions are purified to remove labeled ddNTPs, unused primers, and other reaction components that may interfere with capillary electrophoresis. Purification is achieved using sodium acetate/ethanol or isopropanol precipitation. Purified DNA is resuspended in formamide.

Capillary Electrophoresis

The purified cycle sequencing product is analyzed using a capillary-based Genetic Analyzer. DNA products are separated on the basis of their size with smaller products traveling faster than larger ones. Because each ddNTP base-type is labeled with a unique fluorophore, the sequence of the DNA target can be determined by the order in which the fluorescently-labeled DNA products pass by the exciter/detector cell in the Genetic Analyzer.[6]

Data Analysis

Each specimen can have up to four different primer reads (samples). The SeqScape program is used to assemble a contig from up to four different reads and analyze the data. The resulting consensus sequence may be exported and analyzed using web-based analysis programs, such as Evivar or Genafor.

Reagents

Rare reagents include the five different oligonucleotides found in the Oligo Mix and/or Sequencing Primers A-D as well as the thermostable AmpliTaq Gold.

HBV Sequencing Reagent Kit (List No. 3N03-90)

(1) HBV Pol PCR Mix (3N03Llbl) (1 vial, approximately 1.55 mL, for 48 reactions), 19.447 mM Tris-HCl, pH 8.3, 97.235 mM KCl, 0.097 mM EDTA, 0.389 mM each of dATP, dCTP, dGTP, dTTP, 0.194 mM dUTP, 0.486 uM HBVFP180-204 (5' TAGGACCCCTGCTCGTGTTACA-GGC 3'; SEQ ID NO:1), 0.486 uM HBVRP1202-1178 (5' GTGGGGGTTGCGTCAGCAAACACTT 3'; SEQ ID NO:2), 0.778 uM Quasar-HBVPb250-272 (5' Quasar/AGACTCGTGGTGGACTTCTCTCA/BHQ2 Quencher 3'; SEQ ID NO:5), 0.039 uM Rox dye, 0.085% Sodium Azide, 0.147% Proclin 950, molecular biology grade water.

(2) AmpliTaq Gold Enzyme (3N03Tlbl) (1 vial, 0.078 mL), recombinant themostable AmpliTaq Gold. 5 units/ul.

(3) Activation Reagent (3N03Mlbl) 1 vial (0.778 mL), 38 mM Magnesium Chloride, 30 mM Tris-HCl, pH 8.0, 100 mM KCl, 0.150% Proclin 950, 0.084% Sodium Azide, and molecular biology grade water.

(4) Uracil-DNA-Glycosylase (3N03UNGlbl) (1 vial, 0.060 mL), recombinant UNG. 1 unit/ul.

(5) BigDye Terminator v3.1 Cycle Sequencing Ready Reaction Mix (3N03BDYElbl) (1 vial, 0.9 mL)

(6) HBV Sequencing Pol Primer A (3N03Albl) (1 vial, approximately 0.13 mL, for 48 reactions), 3.2 uM HBVFP180-204 primer (5' TAGGACCCCTGCTCGTGT-TACAGGC 3'; SEQ ID NO:1) in Tris-EDTA buffer.

(7) HBV Sequencing Pol Primer B (3N03BigDyelbl) (1 vial, approximately 0.13 mL, for 48 reactions), 3.2 uM HBVFP420-450 primer (5' TATGCCTCATCTTCTTGTTG-GTTCTTCTGGA 3'; SEQ ID NO:3) in Tris-EDTA buffer.

(8) HBV Sequencing Pol Primer C (3N03Clbl) (1 vial, approximately 0.13 mL, for 48 reactions), 3.2 uM HBVRP704-673 primer (5' CGAACCACTGAACAAATG-GCACTAGTAAACTG 3'; SEQ ID NO:4) in Tris-EDTA buffer.

(9) HBV Sequencing Pol Primer D (3N03Dlbl) (1 vial, approximately 0.13 mL, for 48 reactions), 3.2 uM HBVRP1202-1178 primer (5' GTGGGGGTTGCGTCAG-CAAACACTT 3'; SEQ ID NO:2) in Tris-EDTA buffer.

HBV Sequencing Control Kit (List No. 3N03-80)

(1) Abbott HBV Sequencing Negative Control (4 vials, 1.3 mL per vial). Negative human plasma tested and found to be nonreactive for HBsAg, HIV RNA, anti-HIV-1/HIV-2, HBV DNA, HCV RNA, and anti-HCV by FDA licensed tests. Preservatives: 0.1% ProClin 300 and 0.15% ProClin 950.

(2) Abbott HBV Sequencing Positive Control (4 vials, 1.3 mL per vial). Heat-Inactivated HBV Virus Stock diluted to 4.477 log IU/mL in negative human plasma (when manufactured, the negative plasma was tested, and found to be non-reactive for HBsAg, HIV RNA, anti-HIV-1/HIV-2, HBV DNA, HCV RNA, and anti-HCV by FDA licensed tests). Preservatives: 0.1% ProClin 300 and 0.15% ProClin 950.

Specimen Collection, Storage, and Transport to the Test Site

Specimen Collection and Storage

Human serum and plasma (ACD, EDTA, and CPD) specimens may be used with the HBV Sequencing assay. Freshly drawn specimens (whole blood) can be held at 2 to 30° C. for up to 6 hours prior to centrifugation. After centrifugation, remove serum or plasma from cells. Serum or plasma specimens may be stored: at 15 to 30° C. for up to 24 hours; at 2 to 8° C. for up to 3 days; or at −10° C. or colder for longer term.

Multiple freeze-thaw cycles should be avoided. If frozen, thaw specimens at 15 to 30° C. or at 2 to 8° C. Once thawed, if specimens are not being processed immediately, they can be stored at 2 to 8° C. for up to 6 hours.

HBV Sequencing Assay Procedure

Work Areas

Use three dedicated areas within the laboratory for performing the HBV Sequencing assay.

The Sample Preparation Area is dedicated to processing samples (specimens and HBV Sequencing Controls), and to adding processed samples and controls to the Abbott 96-Well Optical Reaction Plate. After manual preparation of the amplification master mix, it is distributed to the reaction plate. All reagents used in the Sample Preparation Area should remain in this dedicated area at all times. Laboratory coats, pipettes, pipette tips, and vortexers used in the Sample Preparation Area should remain in this area and not be moved to the Amplification Area. Do not bring amplification product into the Sample Preparation Area.

The Amplification Area is dedicated to PCR amplification. Laboratory coats and equipment used in the Amplification Area should remain in this area and not be moved to the other areas.

The Sequencing Area is dedicated to gel electrophoresis, amplified product purification, cycle sequencing, and sequence analysis. Laboratory coats and equipment used in the Sequencing Area should remain in this area and not be moved to the other areas.

Sample Preparation Area

All specimen storage and preparation should take place in the dedicated Sample Preparation Area. Specimen preparation can be performed using m2000sp or m24sp.

Specimen Preparation Performed Using m2000sp

1. A total of 48 samples can be processed in each run. A negative control and a positive control must be included in each run, therefore allowing a maximum of 46 specimens to be processed per run. Check sample volume. Refer to the m2000sp Operations Manual and QUICK REFERENCE GUIDE FOR SAMPLE TUBE SIZES AND VOLUMES for recommended sample input volume. If frozen, thaw specimens at 15 to 30° C. or at 2 to 8° C. Once thawed, if specimens are not being processed immediately, store at 2 to 8° C. for up to 6 hours. Before use, vortex specimens three times for 2 to 3 seconds. Ensure that bubbles or foam are not created. If found, remove them with a new sterile pipette tip for each tube. Specimens showing particulate matter or turbidity should be clarified by centrifugation at 2000 g for 5 minutes prior to testing. Aliquot each specimen into clean tubes or vials if necessary. Refer to the Abbott m2000sp Operations Manual for tube sizes. Avoid touching the inside of the cap when opening tubes.

2. Thaw assay controls at 15 to 30° C. or at 2 to 8° C. Once thawed, if controls are not being processed immediately, store at 2 to 8° C. for up to 24 hours. Vortex each control three times for 2 to 3 seconds before use. Ensure that bubbles or foaming are not created. If found, remove them with a new sterile pipette tip for each tube. Ensure that the contents of the vials are at the bottom after vortexing by tapping the vials on the bench to bring liquid to the bottom of the vials.

3. Thaw amplification reagents at 15 to 30° C. or at 2 to 8° C. until required for the amplification master mix procedure. This step can be initiated before completion of the sample preparation procedure. Note: Do not vortex the amplification reagents. Once thawed, the amplification reagents can be stored at 2 to 8° C. for up to 24 hours if not used immediately.

4. Open the Abbott Proteinase K reagent pack. Add 17.15 mL of Molecular Biology Grade water to a 50 mL polypropylene centrifuge tube. Pipet 2.45 mL of Proteinase K into the container of water. Mix by gentle inversion 10 to 15 times. Transfer the entire contents to a reagent vessel labeled with the Proteinase K barcode label. Place the reagent vessel in reagent carrier #1 location 2. NOTE: Use one bottle of Proteinase K solution and one set of mSample$_{DNA}$ reagents to support up to 24 reactions. Use a second set of Proteinase K and mSample$_{DNA}$ reagents to support 25 to 48 reactions, with the exception of the mMicroparticles. One bottle of mMicroparticles will support up to 48 reactions.

5. Open the Abbott mSample Preparation pack. If crystals are observed in any of the reagent bottles upon opening, allow the reagents to equilibrate at room temperature until the crystals disappear. Do not use the reagents until the crystals have dissolved.

6. Prepare the mWash2$_{DNA}$ by adding 70 mL of USP Grade 190-200 Proof Ethanol (95-100% Ethanol) to the mWash2$_{DNA}$ bottle as described in the Abbott mSample Preparation System$_{DNA}$ product information. Do not use ethanol that contains denaturants.

7. Gently invert the Abbott mSample Preparation$_{DNA}$ bottles to ensure a homogeneous solution and pour the contents into the appropriate reagent vessels per the Abbott m2000sp Operations Manual, Operating Instructions.

8. Place the negative control, the positive control, and the patient specimens into the m2000sp sample rack.

9. Place the 5 mL Reaction Vessels into the m2000sp 1 mL subsystem carrier.

10. Load the carrier racks containing the Abbott mSample Preparation$_{DNA}$ reagents and Proteinase K, and the Abbott 96-Deep Well Plate, on the Abbott m2000sp worktable as described in the Abbott m2000sp Operations Manual.

11. From the Run Sample Extraction screen, select the appropriate application file. Initiate the sample extraction protocol as described in the m2000sp Operations Manual, Operating Instruction. Following sample scan, if samples are not labeled with barcodes, manually enter the Sample IDs for those samples.

12. Sample eluates may be stored for up to 7 days at −10° C. or colder.

Sample Preparation Performed Using m24sp

13. A total of 18 samples can be processed in each run. A negative control and a positive control must be included in each run, therefore allowing a maximum of 16 specimens to be processed per run. Check sample volume. Refer to the m24sp Operations Manual for recommended sample input volume. If frozen, thaw specimens at 15 to 30° C. or at 2 to 8° C. Once thawed, if specimens are not being processed immediately, store at 2 to 8° C. for up to 6 hours. Before use, vortex specimens three times for 2 to 3 seconds. Ensure that bubbles or foam are not created. If found, remove them with a new sterile pipette tip for each tube. Specimens showing particulate matter or turbidity should be clarified by centrifugation at 2000 g for 5 minutes prior to testing. Aliquot each specimen into clean tubes or vials if necessary. Refer to the Abbott m24sp Operations Manual for tube sizes. Avoid touching the inside of the cap when opening tubes.

14. Thaw assay controls at 15 to 30° C. or at 2 to 8° C. Once thawed, if controls are not being processed immediately, store at 2 to 8° C. for up to 24 hours. Vortex each control three times for 2 to 3 seconds before use. Ensure that bubbles or foaming are not created. If found, remove them with a new sterile pipette tip for each tube. Ensure that the contents of the vials are at the bottom after vortexing by tapping the vials on the bench to bring liquid to the bottom of the vials.

15. Thaw amplification reagents at 15 to 30° C. or at 2 to 8° C. until required for the amplification master mix procedure. This step can be initiated before completion of the sample preparation procedure. Note: Do not vortex the amplification reagents. Once thawed, the amplification reagents can be stored at 2 to 8° C. for up to 24 hours if not used immediately.

16. Open the Abbott Proteinase K reagent pack. Add 17.15 mL of Molecular Biology Grade water to a 50 mL polypropylene centrifuge tube. Pipet 2.45 mL of Proteinase K into the container of water. Mix by gentle inversion 10 to 15 times. Calculate the volume of Proteinase K solution required for the m24sp run: (425 uL×number of samples)+1.0 mL for dead volume. Pipet the required volume into a Master Mix Tube (list number 04J71-80).

17. Open the Abbott mSample Preparation pack to check for crystals. If crystals are observed in any of the reagent bottles, allow the reagent to equilibrate at room temperature until the crystals disappear. Do not use the reagents until the crystals have dissolved.

18. Prepare the mWash2$_{DNA}$ by adding 70 mL of USP Grade 190-200 Proof Ethanol (95-100% Ethanol) to the mWash2$_{DNA}$ bottle as described in the Abbott mSample Preparation System$_{DNA}$ product information. Do not use ethanol that contains denaturants. Invert the bottle to mix the contents. If reusing the mSample Preparation SystemDNA reagents, mark the mWash2$_{DNA}$ bottle to indicate that ethanol has already been added.

19. Load the Controls and patient specimens in the m24sp sample rack(s), starting with Position 3 of the IC Sample Rack. Place the Master Mix Tube containing the Proteinase K solution in the last position (16) of Sample Rack 2. CAUTION: Do NOT skip any positions in a sample rack except Position 1 and 2 of the IC Sample Rack. Load controls and specimens into the sample racks in consecutive positions, starting with Position 3 of the IC Sample Rack. Fill all positions in the IC Sample Rack before loading specimens into Sample Rack 2. Insert specimen and control tubes into sample racks carefully to avoid splashing. Ensure that each tube is placed securely in the sample rack so that the bottom of the tube reaches the inside bottom of the rack. Load filled sample racks on the worktable, starting with the IC Sample Rack in worktable Position 1.

20. For each sample to be run, place one 5 mL Reaction Vessel into the Secondary Heat Block and one 1.5 mL Reaction Vessel in the m24sp TeMagS Carrier.

21. Load 1.5 mL Output Tubes or a 96 Deep-Well Plate onto the Output Location of the worktable. Load full racks of pipette tips in the DiTi Carriers and place them on the worktable. Place an empty tip rack and a clean deep-well plate on the Reuse Rack.

22. Remove the caps from the mSample Preparation SystemDNA reagents except the mMicroparticlesDNA bottle. Store the caps on a clean, absorbent surface in the event that recapping is needed after the run. Place the uncapped reagent bottles in their designated positions in the Reagent Carrier. Load the Reagent Carrier on the worktable.

23. Ensure all caps have been removed from specimens, controls, and the Proteinase K solution Master Mix Tube prior to starting the m24sp run. Select an HBV Sequencing m24sp assay script (m24sp Database v 4.0 or higher) appropriate for the desired output vessel: m24sp_HBVSeq_DNA_0.5 mL_Tube; m24sp_HBVSeq_DNA_0.5 mL_DWP. Initiate the m24sp sample extraction protocol as described in the Abbott m24sp Operations Manual, Operating Instructions section.

24. When prompted, vigorously mix the mMicroparticles$_{DNA}$ to fully resuspend them. Uncap and immediately place the mMicroparticlesDNA bottle in the Reagent Carrier and continue the run. Store the cap on a clean, absorbent surface in the event that recapping is needed after the run.

25. When m24sp sample preparation is finished and if not immediately proceeding with the Master Mix Addition Protocol in Package Insert, cap the 1.5 mL Output Tubes or cover the 96 Deep-Well Plate and store at 2 to 30° C. for 4 hours, or at −10° C. or colder for up to 7 days.

26. At the end of each run, remove the remaining reagents from the m24sp worktable. The Abbott mSample PreparationDNA reagents may be used a maximum of 3 times over 14 days for up to 24 reactions when stored tightly capped at 15 to 30° C. The Proteinase K solution Master Mix Tube and any remaining solution in the tube must be discarded. Follow the appropriate laboratory guidelines for disposal. Any remaining Proteinase K solution in the 50 mL polypropylene centrifuge tube (prepared in Step 3 of the ASSAY PROTOCOL section) may be used two more times over 14 days when stored tightly capped at 2 to 8° C.

Amplification Area

Switch on and initialize the Abbott m2000rt in the amplification area. The Abbott m2000rt requires 15 minutes to warm up. NOTE: Remove gloves before returning to the Sample Preparation Area.

Sample Preparation Area

NOTE: Change gloves before handling the amplification reagents.

27. After sample preparation is completed, manually assemble the HBV Sequencing assay Master Mix. Thaw Amplification Reagents at 2 to 8° C. or at 15 to 30° C. Once thawed, reagents may be stored at 2 to 8° C. for up to 24 hours prior to use. Amplification reagents may be used up to three times after freeze-thaw. Prior to opening the amplification reagents, ensure that the contents are at the bottom of the vials by tapping the vials in an upright position on the bench and mix the HBV Pol PCR Mix and Activation Reagent vials. Combine the following volumes of reagents in a sterile, 1.7 mL microcentrifuge tube:

| Reagent | Volume for 1 Reaction (µL) |
| --- | --- |
| HBV Pol PCR Mix | 25.711 |
| UNG | 0.500 |
| AmpliTaq Gold Enzyme | 0.500 |
| Activation Reagent | 3.289 |

Note:
If using m2000sp for automated mastermix dispense, make five additional reactions-worth to compensate for process loss. Vortex the Master Mix (i.e. combined 4 reagents in table above) for 3 to 5 seconds to mix. Transfer the entire contents of the microcentrifuge tube to a clean m2000 Master Mix Tube.

28. Select the appropriate deep well plate from the Run Master Mix Addition screen that matches the corresponding sample preparation extraction. Initiate the Abbott m2000sp Master Mix Addition protocol. Follow the instructions as described in the Abbott m2000sp Operations Manual, Operating Instructions section. Note: If setting-up the PCR plate manually, add 30 ul of mastermix to each well to be used and 20 ul of each purified sample. On m2000rt, under Sample Type, select Control. Then select "HBVSEQ_NEG" for the negative control and "HBVSEQ_POS" for the positive control. Subsequently, under Sample Type, select Patient. Then manually enter the Sample IDs for those samples. The m2000rt protocol (step 31) must be started within 90 minutes of assembling the PCR Master Mix (step 27).

29. Place the 96-Well Optical Reaction Plate into the Splash-Free Support Base for transfer to the thermal cycler.

30. Seal the Abbott 96-Well Optical Reaction Plate after the Abbott m2000sp instrument has completed addition of samples and master mix according to the Abbott m2000sp Operations Manual, Operating Instructions section.

31. Export the completed 96-Well Optical Reaction Plate results to a CD.

Amplification Area

32. Place the Abbott 96-Well Optical Reaction Plate in the Abbott m2000rt instrument. Import the m2000sp test order via CD per the Import Order instructions in the Abbott m2000rt Operations Manual, Operating Instructions section. After loading the plate, select "Start" to start the run. The following thermal cycling parameters will be executed.

| Stage | Amplification Parameters | Number of Cycles |
| --- | --- | --- |
| 1 | 50° C. for 10 min | 1 |
| 2 | 95° C. for 10 min | 1 |
| 3 | 95° C. for 20 sec<br>65° C. for 45 sec<br>66° C. for 2 min | 45 |
| 4 | 72° C. for 10 min | 1 |
| 5 | 4° C. hold | 1 |

Note:
At the end of stage 3, the following message appears: "6304: PCR data acquisition complete. Run can be stopped at any time. Initiating hold." Ignore this message until stage 4 is complete. Confirm that the sample temperature has reached 4° C. before stopping the run.
Note:
Do not leave plate on hold for more than 24 hours. The residual UNG activity may degrade the amplified DNA.
Note:
Thermal cycling may be performed using a PE 9700, or equivalent. If so, program the thermal cycling parameters (making sure that the reaction volume is set to 50 uL and the ramp speed is set to PE 9600 mode), place the sealed plate into the cycler, apply a MicroAmp Optical Film Compression Pad on top of the plate, close the cycler lid and start the program.

33. Remove the 96-Well Reaction Plate from the m2000rt and seal in a zip-lock bag for further processing. The 96-Well Reaction Plate may be stored at −10° C. or colder for up to 7 days before purification (in the Sequencing Area).

Sequencing Area

34. Gel electrophoresis is required only if PCR amplification was not performed using m2000rt. To perform gel electrophoresis:
   a. If frozen, thaw the DNA mass ladder and the purified samples.
   b. Prepare a 1% agarose gel in 1×TAE buffer containing 0.5 ug/mL of ethidium bromide. Ensure that the wells can hold 6 uL of sample.
   c. Pour sufficient 1×TAE buffer, containing 0.5 ug/mL of ethidium bromide, to cover the gel.
   d. Remove the gel comb.
   e. In separate tubes, mix 5 uL of each sample and 1 uL gel loading buffer.
   f. Mix 1 uL low DNA mass ladder, 4 uL water, and 1 uL gel loading buffer.
   g. Load the lanes with as follows: lane 1 6 uL of the DNA ladder, lanes 2-onwards 6 uL of each sample.

| Band | Fragment Size (kb) | Amount of DNA (ng) 1 µL Ladder |
| --- | --- | --- |
| 1 | 2.0 | 50 |
| 2 | 1.2 | 30 |
| 3 | 0.8 | 20 |
| 4 | 0.4 | 10 |
| 5 | 0.2 | 5 | h. Electrophorese at 10 V/cm until the blue dye has migrated at least 5 cm from the wells.
   i. Examine the gel with UV light.
   j. Record the image using an exposure time that does not saturate the film and shows the differences in intensity of the mass ladder fragments.
   k. Examine each sample result. If a major band is found between Band 2 (1.2 kb) and Band 3 (0.8 Kb) of the DNA size marker, the sample is considered successfully amplified. It is acceptable if bands 4 and 5 are not visualized.

35. There are two preferred choices for purification of PCR products: ExoSAP-IT or QIAGEN QIAquick:
   a. To purify using ExoSAP-IT,
      (1) Program the PE 9700 thermal cycler or equivalent with the following thermal cycling parameters (making sure that the reaction volume is set to 50 uL and the ramp speed is set to PE 9600 mode), place the sealed plate into the cycler, apply a MicroAmp Optical Film Compression Pad on top of the plate, close the cycler lid and start the program.

| Stage | Parameters | Number of Cycles |
| --- | --- | --- |
| 1 | 37° C. for 15 min | 1 |
| 2 | 80° C. for 15 min | 1 |

(2) On a new 96 well plate, add 4 ul of ExoSAP-IT into as as many wells as samples to be processed.
      (3) Add 10 ul of each PCR product to its own well containing ExoSAP-IT.
      (4) Seal the plate before vortexing it for 3 to 5 seconds.
      (5) Centrifuge the plate for 5 to 10 seconds at 2,000 xg.
      (6) Place the plate into thermal cycler, apply a MicroAmp Optical Film Compression Pad on top of the plate, close the cycler lid and start the program.

b. To purify using QIAGEN QIAquick,
   (1) Add 250 uL of Buffer PB to each sample.
   (2) Transfer each mixture to a spin column. Place each spin column into a collection tube.
   (3) Centrifuge for 1 min. at 13,000 rpm.
   (4) Discard waste from each collection tube and place the spin column back into the same collection tube.
   (5) Add 750 uL of Buffer PE to each spin column. (If a new bottle of Buffer PE is used, the PE Buffer concentrate must be mixed with 100% ethanol prior to use. Add 220 mL 100% ethanol to the bottle contents. Cap the bottle and invert it 8 times to mix.) Place each spin column into a collection tube.
   (6) Centrifuge for 1 min. at 13,000 rpm.
   (7) Transfer each spin column into a labeled 1.5 mL or 1.7 mL microcentrifuge tube.
   (8) Add 50 ul buffer PE to each tube.
   (9) Centrifuge for 1 min. at 13,000 rpm.
   (10) Discard spin columns and then cap the tubes.

36. After purification, process the samples immediately (ExoSAP-IT and Qiagen) or store at −10° C. or colder for up to 7 days (Qiagen only).

37. To determine if samples require dilution, refer to the "Interpretation" column of the m2000rt Results log or list. If the Interpretation reads "Not detected See Package Insert," the sample did not amplify appropriately and therefore should not be taken forward in the assay process. If the Interpretation reads "Dilute 1:2", then add 10 uL water (Ultrapure) to 10 uL of the sample. If the Interpretation reads "Dilute 1:5", then add 40 uL water (Ultrapure) to 10 uL of the sample. After all samples have been appropriately diluted, vortex for 3 to 5 seconds using a vortex mixer set to 1,700 rpm. Note: If PCR was performed using the PE 9700, or equivalent, and subsequent gel electrophoresis, then examine the presence of a major PCR product band between 1.2 and 0.8 kb (i.e. band 2 and band 3 from the top of the DNA mass ladder). Other minor band(s) of less intensity are acceptable. If the major PCR product band intensity is ≥20 ng relative to the DNA mass ladder, dilute the sample 1:10. If a band is visible, but of <20 ng intensity, high quality sequence may not be obtained.

38. To perform cycle sequencing, do the following
   a. Thaw Sequencing Primers at 2 to 8° C. or at 15 to 30° C. Once thawed, primers may be stored at 2 to 8° C. for up to 24 hours prior to use. Sequencing Primers may be used up to three times after freeze-thaw.
   b. Prior to opening the Sequencing Primer bottles, mix them and then ensure that the contents are at the bottom of the vials by tapping the vials in an upright position on the bench.
   c. Combine the following volumes of reagents in a sterile, 1.7 mL microcentrifuge tube.

| Component | Volume Needed for 1 Sample (uL) |
|---|---|
| BigDye Terminator v3.1 Cycle Sequencing RR-100 | 4.0 |
| Primer A, B, C, or D | 2.0 |
| Total Volume | 6.0 |

NOTE: Make additional reactions to compensate for pipetting loss.

39. Use the following diagram to aid in the addition of cycle sequencing reaction mixtures to a 96-well reaction plate (for 96 reactions).

|   | 1 | 2 | 3 | 4 | 5 | 6 | 7 | 8 | 9 | 10 | 11 | 12 |
|---|---|---|---|---|---|---|---|---|---|---|---|---|
| A | A | A | A | A | A | A | A | A | A | A | A | A |
| B | B | B | B | B | B | B | B | B | B | B | B | B |
| C | C | C | C | C | C | C | C | C | C | C | C | C |
| D | D | D | D | D | D | D | D | D | D | D | D | D |
| E | A | A | A | A | A | A | A | A | A | A | A | A |
| F | B | B | B | B | B | B | B | B | B | B | B | B |
| G | C | C | C | C | C | C | C | C | C | C | C | C |
| H | D | D | D | D | D | D | D | D | D | D | D | D |

Pipette 6.0 uL of cycle sequencing Master Mix A into the appropriate number of wells in rows A and E. Pipette 6.0 uL of cycle sequencing Master Mix B into the appropriate number of wells in rows B and F. Pipette 6.0 uL of cycle sequencing Master Mix C into the appropriate number of wells in rows C and G. Pipette 6.0 uL of cycle sequencing Master Mix D into the appropriate number of wells in rows D and H.

40. Use the following diagram to aid in the addition of samples to a 96-well reaction plate (for 96 reactions).

|   | 1 | 2 | 3 | 4 | 5 | 6 | 7 | 8 | 9 | 10 | 11 | 12 |
|---|---|---|---|---|---|---|---|---|---|---|---|---|
| A | PC | S2 | S4 | S6 | S8 | S10 | S12 | S14 | S16 | S18 | S20 | S22 |
| B | PC | S2 | S4 | S6 | S8 | S10 | S12 | S14 | S16 | S18 | S20 | S22 |
| C | PC | S2 | S4 | S6 | S8 | S10 | S12 | S14 | S16 | S18 | S20 | S22 |
| D | PC | S2 | S4 | S6 | S8 | S10 | S12 | S14 | S16 | S18 | S20 | S22 |
| E | S1 | S3 | S5 | S7 | S9 | S11 | S13 | S15 | S17 | S19 | S21 | S23 |
| F | S1 | S3 | S5 | S7 | S9 | S11 | S13 | S15 | S17 | S19 | S21 | S23 |
| G | S1 | S3 | S5 | S7 | S9 | S11 | S13 | S15 | S17 | S19 | S21 | S23 |
| H | S1 | S3 | S5 | S7 | S9 | S11 | S13 | S15 | S17 | S19 | S21 | S23 |

Pipette 4.0 uL of the Positive Control into wells A1, B1, C1, and D1. Pipette 4.0 uL of the first sample (S1) into wells E1, F1, G1, and H1. Continue adding 4.0 uL of the samples to the remaining columns according to the plate diagram Note: the Negative Control and any samples that did not amplify should not be taken through cycle sequencing; only the Positive Control and reactive samples should be sequenced.

41. Seal the 96-Well PCR Reaction Plate with an optical adhesive cover.

42. Program and run the PE 9700 thermal cycler or equivalent as shown below (ensure that 9600 emulation mode is used during cycle sequencing; the alternative, Max, will result in poor quality sequencing data).

| Stage | Cycle Sequencing Parameters | Number of Cycles |
|---|---|---|
| 1 | 96° C. for 1 min | 1 |
| 2 | 96° C. for 10 sec<br>50° C. for 5 sec<br>60° C. for 4 min | 25 |
| 3 | 4° C. hold | 1 |

43. Do not store the samples at 4° C. on the thermal cycler for longer than 24 hours. Samples can be stored at −10° C. or colder for up to three days.

44. There are two preferred choices to to purify cycle sequencing products: sodium acetate-ethanol precipitation and isopropanol precipitation.
   a. To purify using sodium acetate-ethanol precipitation
      (1) Add 26 uL of freshly prepared ethanol/sodium acetate solution to each well (to make this solution, for each reaction combine 1 uL of 3M sodium acetate, pH 5.2, and 25 uL of 100% ethanol).
      (2) Seal the plate with an optical adhesive cover.
      (3) Vortex the plate for 1 minute.
      (4) Centrifuge the plate for 20 minutes at 2,000×g.
      (5) As soon as the centrifuge stops, carefully remove the optical adhesive cover without disturbing the pellets.
      (6) Immediately place an absorbent paper towel on top of the plate and invert it.
      (7) Place the plate in the centrifuge in the inverted position, on top of paper towel, and centrifuge for 1 minute at 150×g.
      (8) Add 75 uL 70% ethanol to each well.
      (9) Centrifuge the plate for 5 minutes at 2,000×g.
      (10) Immediately place an absorbent paper towel on top of the plate and invert it.
      (11) Place the plate in the centrifuge in the inverted position, on top of paper towel, and centrifuge for 1 minute at 150×g.
      (12) Analyze immediately or seal the plate with an optical adhesive cover and store at −10'C or colder in the dark for up to 7 days.
   b. To purify using isopropanol precipitation
      (1) Add 40 uL of freshly prepared 75% isopropanol solution to each well (to make this solution, for each reaction combine 30 uL of 100% isopropanol and 10 uL of deionized water).
      (2) Seal the plate with an optical adhesive cover.
      (3) Vortex the plate for 1 minute.
      (4) Centrifuge the plate for 45 minutes at 1,700×g.
      (5) As soon as the centrifuge stops, carefully remove the optical adhesive cover without disturbing the pellets.
      (6) Immediately place an absorbent paper towel on top of the plate and invert it.
      (7) Place the plate in the centrifuge in the inverted position, on top of paper towel, and centrifuge for 1 minute at 700×g.
      (8) When the centrifuge stops and drying is complete, analyze the plate immediately or seal the plate and store it at −10° C. or colder in the dark for up to 7 days 45. To perform electrophoresis on the AB Genetic Analyzer 3130/3130xl perform the following. Note: These instructions assume that the AB Genetic Analyzer 3130/3130xl computer is loaded with SeqScape software, version 2.5 or later, and has the "HBV_SEQv2" project template, described below, already entered. The project template file has been provided on the HBV Sequencing Application CD-ROM and can be imported directly into SeqScape. Alternatively, the project template may be created manually by entering the parameters listed below (see SeqScape User Guide version 2.5 or later, AB Part Number 4359442). Note: The templates assume the use of POP7 and Big Dye v3.1.

| Protocol/Other | Tab | Type of Setting | Setting |
|---|---|---|---|
| Analysis Protocol | General | Name | HBV_SEQ |
| | Basecalling | Basecaller | KB.bcp |
| | | DyeSet/Primer | KB_3130_POP7_BDTv3.mob |
| | | Processed Data | True Profile |
| | | Quality Threshold | Do not assign N's to Basecalls |
| | Mixed Bases | Mixed Bases | Select. Use Mixed Base Identification<br>Call IUB if 2nd highest peak is ≥30% |
| | Clear Range | Use quality values | Select. Remove bases from the ends until fewer than 4 bases out of 20 have QVs < 20 |
| | | Use reference trimming | Select. |
| | Filter | Maximum Mixed Bases (%) | 20.0 |
| | | Maximum Ns (%) | 10.0 |
| | | Minimum Clear Length (bp) | 50 |
| | | Minimum Sample Score | 20 |
| Analysis Defaults | General | Analysis Defaults Name | HBV_SEQ |
| | Project | Gap Penalty | 30.0 |
| | | Extension Penalty | 1.0 |
| | | Couple the amino acid alignment to the nucleotide alignment | Select |
| | Specimen | Gap Penalty | 22.5 |
| | | Extension Penalty | 8.5 |
| | | # Library Matches | 20 |
| | | Basecall Samples | Select |
| | Sample | Analysis Protocol | HBV_SEQ |
| | | Always use this analysis protocol | Select |

| Protocol/Other | Tab | Type of Setting | Setting | | | |
|---|---|---|---|---|---|---|
| Display Settings Reference Data Group | DefaultDisplaySetting General | Default Reference Data Group Name | Select HBV_SEQv2 | | | |
| | | Codon Table | Standard | | | |
| | ROI | Layer Reference: National Center for Biotechnology Information (NCBI) reference genotype A: X70185 | 1-3221 | | | |
| | | Layer Drug Resistance | 130-1161 w/Translation | | | |
| | | Layer Validity Range | 337-909 w/Translation | | | |
| | NT Variants | Layer | Position | Reference | Variant | Description |
| | | Drug Resistance | 238 | T | A | 238A |
| | | | 238 | T | G | 238G |
| | | | 506 | T | C | 506C |
| | | | 517 | G | C | 517C |
| | | | 517 | G | T | 517T |
| | | | 538 | T | A | 538A |
| | | | 539 | T | G | 539G |
| | | | 540 | G | C | 540C |
| | | | 540 | G | T | 540T |
| | | | 541 | G | A | 541A |
| | | | 541 | G | T | 541T |
| | | | 542 | C | T | 542T |
| | | | 550 | A | C | 550C |
| | | | 550 | A | G | 550G |
| | | | 550 | A | T | 550T |
| | | | 551 | C | G | 551G |
| | | | 551 | C | T | 551T |
| | | | 552 | T | G | 552G |
| | | | 580 | G | A | 580A |
| | | | 604 | A | G | 604G |
| | | | 604 | A | T | 604T |
| | | | 605 | G | T | 605T |
| | | | 610 | A | G | 610G |
| | | | 610 | A | T | 610T |
| | | | 611 | T | C | 611C |
| | | | 611 | T | G | 611G |
| | | | 612 | G | A | 612A |
| | | | 612 | G | C | 612C |
| | | | 612 | G | T | 612T |
| | | | 641 | T | C | 641C |
| | | | 643 | C | T | 643T |
| | | | 644 | A | C | 644C |
| | | | 697 | A | G | 697G |
| | | | 707 | A | C | 707C |
| | | | 748 | A | C | 748C |
| | | | 748 | A | G | 748G |
| | | | 750 | G | A | 750A |
| | | | 750 | G | C | 750C |
| | | | 750 | G | T | 750T |
| | AA Variants | Layer | AA position | Reference | Variant | Description |
| | | Drug Resistance | 80 | L | I | 80I |
| | | | 80 | L | V | 80V |
| | | | 169 | I | T | 169T |
| | | | 173 | V | L | 173L |
| | | | 180 | L | C | 180C |
| | | | 180 | L | M | 180M |
| | | | 181 | A | S | 181S |
| | | | 181 | A | T | 181T |
| | | | 181 | A | V | 181V |
| | | | 184 | T | A | 184A |
| | | | 184 | T | C | 184C |
| | | | 184 | T | F | 184F |
| | | | 184 | T | G | 184G |
| | | | 184 | T | I | 184I |
| | | | 184 | T | L | 184L |
| | | | 184 | T | M | 184M |
| | | | 184 | T | S | 184S |
| | | | 194 | A | T | 194T |
| | | | 202 | S | C | 202C |
| | | | 202 | S | G | 202G |

-continued

| Protocol/Other | Tab | Type of Setting | Setting | | | |
|---|---|---|---|---|---|---|
| | | | 202 | S | I | 202I |
| | | | 204 | M | I | 204I |
| | | | 204 | M | S | 204S |
| | | | 204 | M | V | 204V |
| | | | 214 | V | A | 214A |
| | | | 215 | Q | S | 215S |
| | | | 233 | I | V | 233V |
| | | | 236 | N | T | 236T |
| | | | 250 | M | I | 250I |
| | | | 250 | M | L | 250L |
| | | | 250 | M | V | 250V |
| | Variant Style | Variant Settings | NT Variants: | | | |
| | | | Known change base - Blue | | | |
| | | | Known insertion - Red | | | |
| | | | Known deletion - Black | | | |
| | | | Unknown change base - Green | | | |
| | | | Unknown insertion - Magenta | | | |
| | | | Unknown deletion - Yellow | | | |
| | | | Crucial position - Blue | | | |
| | | | AA Variants | | | |
| | | | Known change residue - Drug Resistant Variant | | | |
| | | | Know insertion - Red | | | |
| | | | Known deletion - Black | | | |
| | | | Unknown change residue - Green | | | |
| | | | Unknown insertion - Magenta | | | |
| | | | Unknown deletion - Yellow | | | |
| | | | Silent mutation - Red | | | |
| Project Templates | HBV_SEQv2 | Reference Data Group | HBV_SEQv2 | | | |
| | | Analysis Defaults | HBV_SEQ | | | |
| | | Display Settings | DefaultDisplaySettings for SeqScape v 2.0 | | | | a1. Power on the monitor. Power on the computer. In the Log on to Windows dialog box: enter the user name and password, click OK. Press the on/off button on the front of the sequencer (make sure that the oven door is closed and locked and the instrument doors are shut before turning on the instrument). Ensure that the green status light is on and not flashing before proceeding. If the green status light does not come on, start the Data Collection software and view the log. Ensure that the daily, weekly, monthly, and as-needed genetic analyzer instrument maintenance tasks have been completed. Ensure that the 50 cm capillary array is on the instrument (each capillary is designed to support a minimum of 100 runs). Replace the POP7 polymer bottle if the bottle has been on the instrument for longer than 7 days. Replace 1× Sequencing Buffer (before each run) up to the respective fill lines in the Anode (position 1 in the tray) and Cathode (next to the POP7 bottle) reservoirs. Replenish the water reservoirs (positions 2 and 4 in the tray) using deionized water.

| Position 2 | Position 4 |
|---|---|
| Water | Water |
| Position 1 | Position 3 |
| 1X Sequencing Buffer | Empty | b1. Remove bubbles in the lines, if present.
c1. Select the Data Collection icon on the computer desktop to start 3130/3130xl Data Collection v3.0. As each application activates, the red circles (off) change to yellow triangles (activating)>, and then to green squares (on) when they are fully functional.
d1. In Data Collection, click+to expand the subfolders in the left tree pane.
e1. In the tree pane of the Data Collection software, click Results Group. Click New. Under the General tab, name the Results Group "HBV_SEQ", add a Results Group Owner and, if desired, a Results Group Comment. Under the Destination tab, provide the Root Destination where the data will be stored. Under Naming tab, under Name Delimiter, select the—delimiter. Click OK. The HBV_SEQ Results Group can be used with all subsequent runs.
f1. In the tree pane of the Data Collection software, click Plate Manager.
g1. Click New to display the New Plate Dialog box.
h1. Type a name for the plate.
i1. Type a description for the plate (optional).
j1. Select SeqScape_YourInstrumentName in the Application drop-down list.
k1. Select 96-well in the Plate Type drop-down list.
l1. Type a name for the owner and operator.
m1. Click OK to open the SeqScape Plate Editor.
n1. In the Sample Name column, enter a sample name for each sample. Use the format: xxxxxxxxxx-A, xxxxxxxxxx-B, xxxxxxxxxx-C, xxxxxxxxxx-D to designate each specimen being sequenced by each sequencing primer.
o1. The Priority column can be manipulated to alter the priority in which a sample is processed. A priority of 100 is assigned automatically. Use a lower priority number to decrease a sample's priority.
p1. In the Comments column, enter any comments for the sample.
q1. In the Project column, select Create New Project. Once the Create New Project window opens, type the name of the project, and select Project Template (HBV_SEQv2). Click OK. The selected Project Template will appear in the Project Template column.
r1. In the Specimen column, create New Specimen ID for each specimen (a specimen consists of four samples). Use the format xxxxxxxxxx for the specimen name.

s1. In the Results Group 1 column, select the HBV_SEQ Results Group.

t1. In the Instrument Protocol 1 column, select New to open the Protocol Editor. Under Name, enter HBV_SEQ. Under Run Module, select BDx_StdSeq50_POP7_1. Under Dye Set, select Z_BigDyeV3. Click OK. This instrument protocol can be used with all subsequent runs.

u1. In the Analysis Protocol 1 column, select New. Create the Analysis Protocol per the following table. The HBV_SEQ Analysis Protocol can be used with all subsequent runs.

| Tab | Type of Setting | Setting |
|---|---|---|
| General | Name | HBV_SEQ |
| Basecalling | Basecaller | KB.bcp |
| | DyeSet/Primer | KB_3130_POP7_BDTv3.mob |
| | Processed Data | True Profile |
| | Quality Threshold | Do not assign N's to Basecalls |
| Mixed Bases | Mixed Bases | Select. Use Mixed Base Identification Call IUB if 2nd highest peak is >30% |
| Clear Range | Use quality values | Select. Remove bases from the ends until fewer than 4 bases out of 20 have QVs < 20 |
| | Use reference trimming | Select. |
| Filter | Maximum Mixed Bases (%) | 20.0 |
| | Maximum Ns (%) | 10.0 |
| | Minimum Clear Length (bp) | 50 |
| | Minimum Sample Score | 20 | v1. Click OK to save then close the plate record. Note: After clicking OK within the SeqScape Plate Editor, the completed plate record is stored in the plate manager database. The plate record can be searched for, edited, exported, or deleted in the Plate Manager.

w1. If present, remove the seal from the plate to be analyzed.

x1. Add 20 uL Hi-Di Formamide to each sample-containing well. The plate is stable for up at 35 hours at room temperature when protected from light.

y1. Seal the plate with an optical adhesive cover.

z1. Vortex for 10 to 15 seconds at 1,700 rpm.

a2. Centrifuge the plate for 30-40 s at 2,000×g.

b2. Remove the optical adhesive cover, and lay a septa flat on the plate.

c2. Align the holes in the septa strip with the wells of the plate then firmly press downward onto the plate.

d2. Place the sample plate into the base plate.

e2. Snap the plate retainer onto the plate and plate base.

f2. Verify that the holes of the plate retainer and the septa are aligned. If not, re-assemble the plate assembly.

g2. Press the Tray button and wait for the autosampler to stop at the forward position.

h2. Open the front doors.

i2. Place the plate assembly on the autosampler in position A or B. Note: There is only one orientation for the plate, with the notched end of the plate base away from the operator.

j2. Ensure the plate assembly fits flat in the autosampler. Failure to do so may allow the capillary tips to lift the plate assembly off of the autosampler.

k2. Close the instrument doors.

l2. In the tree pane of the Data Collection software, click GA Instruments >ga3130xl>Run Scheduler >Plate View.

m2. Click Find All.

n2. Select the plate record to be run.

o2. Click the plate position indicator that matches the plate to be linked. The plate map color will change from yellow to green when it is successfully linked.

p2. In the toolbar of the Data Collection software window, click the green arrow to begin the run.

q2. The processing plates dialog box opens. Click OK.

30. Data Analysis:

a. After the run has completed, open SeqScape.

b. Select File, New Project. Give the project the same name as when setting-up the Data Collection plate record.

c. In the New Project box, type the first few letters of the project template, HBV_SEQv2. Click New.

d. Click File, Import Samples To Project. Find the sequencing files. Click "Use sample name" and then select file(s). Click Auto Add. Click OK.

e. Click the green arrow in the tool bar to initiate analysis.

f. After completion of analysis, select the run (not individual specimens) within the Project Navigator.

g. For the Positive Control, check the following:

(1) In the Active Layer menu, select Layer Drug Resistance. Under Analysis, click Report Manager, then click Specimen Statistics Report. Verify that the number of samples is 3 or greater and the Range on Reference covers nucleotides 337:909.

(2) In the Active Layer menu, select Layer Drug Resistance. Under Analysis, Report Manager, click AA Variants Report. Verify that the Positive Control contains no clinically relevant amino acid variants at RT amino acid positions associated with drug resistance (in the description column of the SeqScape AA Variants Report).

(3) If a clinically relevant mutation is detected, the accuracy of this determination may be checked by clicking on the NT Change column of the AA Variants Report and, in turn, clicking on the Base Change of the Mutations Report. To check the electropherograms of the specimen in question, click on the triangle before the Specimen Name within the Project View. The nucleotide base may be edited if desired (place the cursor on the base in question, press delete, then type in the correct sequence) and the edits are documented in the Audit Trail Report.

(4) If these criteria are not met (once review and editing are complete), consider repeating the run.

h. For each specimen, check the following:

(1) In the Active Layer menu, select Layer Drug Resistance. Under Analysis, click Report Manager, then click Specimen Statistics Report. Verify that the number of samples is 3 or greater and the Range on Reference covers nucleotides 337:909.

(2) In the Active Layer menu bar, selectLayer Drug Resistance for analysis of drug resistance mutations. Under Analysis, Report Manager, click AA Variants Report. Check to determine if the specimen contains clinically relevant amino acid variant/s listed in the Description column. If a clinically relevant mutation is detected, the accuracy of this determination may be checked by clicking on the NT Change column of the AA Variants Report and, in turn, clicking on the Base Change of the Mutations Report. To check the electropherograms of the specimen in question, click on the triangle before the Specimen Name within the Project View. The nucleotide base may be edited if desired (place the cursor on the base in question, press delete, then type in the correct sequence) and the edits are documented in the Audit Trail Report.
h. To export the specimen consensus sequence(s), perform the following:
 (1) To export an entire run containing multiple consensus sequences, open File, select the whole file, click Export.
 (2) To export an individual consensus sequence, open File, select the sequence, click Export. Note: While open, reports such as Specimen Statistics, AA Variants, or Audit Trail Report, may be exported using the same methodology.
i. The specimen consensus sequence(s) may be sent to Evivar-SeqHepB (www.seqhepb.com), or (www.genafor.org, then select geno2pheno [hbv]) for clinical interpretation.

Post Processing Procedures

1. Store samples (unprocessed, post-PCR, post-purification, etc.) as recommended in the procedure.
2. To minimize health hazards, and the potential spread of amplified product, ensure that waste materials (gloves, tips, etc.) are disposed of in sealed bags that are then autoclaved.

Quality Control Procedures

Abbott m2000rt Optical Calibration

Refer to the Calibration Procedures section in the Abbott m2000rt Operations Manual for a detailed description of how to perform an Abbott m2000rt Optical Calibration. Optical calibration of the Abbott m2000rt instrument ensures the accurate measurement and discrimination of dye fluorescence during the HBV Sequencing assay. The following Abbott m2000rt Optical Calibration Plates are used to calibrate the Abbott m2000rtinstrument for the HBV Sequencing assay: Cy5™ Plate (Cyanine) and ROX™ Plate (Carboxy-X-rhodamine). Additionally, please refer to Applied Biosystems 3130/3130xl Genetic Analyzer Manuals for information on how to maintain and calibrate these instruments.

Negative and Positive Controls

A negative control and a positive control are included in each run to evaluate run validity. An error is displayed when a control result is out of range. Refer to the Abbott m2000rt Operations Manual for an explanation of the corrective actions for the error code. If negative or positive controls are out of range, all of the specimens and controls from that run should be reprocessed, beginning with sample preparation. The presence of HBV should not be detected in the negative control. HBV detected in the negative control is indicative of contamination by other samples or by amplified product introduced during sample preparation or during preparation of the Abbott 96-Well Optical Reaction Plate. To avoid contamination, clean the Abbott m2000sp and m2000rt instruments and repeat the sample processing for controls and specimens following the Procedural Precautions. If negative controls are persistently reactive, assume that the laboratory is contaminated.

After completion of PCR, and optional gel electrophoresis, only the Positive Control should be processed further. The Positive Control helps determine whether cycle sequencing and capillary electrophoresis were performed correctly. If the Positive Control is invalid, consider repeating cycle sequencing and/or capillary electrophoresis. The assay is standardized against the World Health Organization (WHO) International Standard for Hepatitis B Virus DNA (NIBSC Code 97/746).[7]

Results

Two types of results are produced:

Post-PCR. This data is used to determine if the sample was amplified correctly, and if so, how the amplified product needs to be diluted prior to cycle sequencing. Follow the m2000 report, Results Interpretation, to determine whether to dilute 1:2 or 1:5. Samples designated as Not detected See Package Insert were not amplified appropriately and should not be processed further. Alternatively, if an m2000rt was not used, amplification success data, and associated dilution, can be obtained using gel electrophoresis.

Post-Sequencing. Nucleotide sequence data are obtained using capillary electrophoresis. SeqScape is used to analyze the DNA sequencing data. Specimen consensus sequence(s) may be sent to Evivar or Genafor for further analysis.

Bibliography

1. Lai L L, Ratziu V, Yuen, M, Poynard T. Viral hepatitis B. Lancet, 2003, 362, 2089-2094.
2. Valsamakis A. Molecular testing in the diagnosis and management of chronic hepatitis B. Clinical Microbiological Reviews 2007, 20: 426-439
3. Zoulim F. Antiviral therapy of chronic hepatitis B. Antiviral Research 2006, 71, 206-215.
4. Boom R, Sol C J A, Heijtink R, et al. Rapid purification of hepatitis B virus DNA from serum. *J Clin Microbiol* 1991; 29(9):1804-11.
5. Read S J. Recovery efficiencies of nucleic acid extraction kits as measured by quantitative LightCycler PCR. *J Clin Pathol: Mol Pathol* 2001; 54:86-90.
6. Murray V. Improved double-stranded DNA sequencing using the linear polymerase chain reaction. *Nucleic Acids Res* 1989; 17:8889.
7. Saldanha J, Gerlich W, Lelie N, et al. An International Collaborative Study to Establish a WHO International Standard for HBV DNA Nucleic Acid Amplification Technology Assay. WHO Expert Committee on Biological Standardization: Fiftieth Report, Geneva, Switzerland; 1999. WHO Technical Report Series No 904; BS/99.1917.

Example 2

Limit of Detection

This Example shows that the above-described assay provides an acceptable limit of detection.

Materials:

| Instrument Platform(s) & #(s): | m2000sp FRE20 and m2000rt CTS-11, CTS-123, VTS-10 (sample prep/PCR)<br>m2000sp FRE37 and m2000rt CTS-11, CTS-123, VTS-10 (sample prep/PCR)<br>PE9700 LC952924, LC952928 (cycle sequencing)<br>3130xl Genetic Analyzer AM02142 (sequence analysis) |
|---|---|

Devices being Verified (Reagents/Calibrators/Controls/Application File):

| Item | List Number Or Code No. |
|---|---|
| HBV Pol PCR Mix | 3N30L |
| Activation Reagent | 51-5032000099 |
| AmpliTaq Gold Enzyme | 337940099 |
| UNG | 6L87-01 |
| HBV Sequencing Negative Control | 60217 |

| Item | List Number Or Code No. |
|---|---|
| HBV Sequencing Positive Control | 3N03W0001 |
| BigDye Terminator v3.1 (ABI) | 4336911 |
| HBV Sequencing Pol Primer A | 3N03A0001 |
| HBV Sequencing Pol Primer B | 3N03B0001 |
| HBV Sequencing Pol Primer C | 3N03C0001 |
| HBV Sequencing Pol Primer D | 3N03D0001 |

| Application File Name | Version |
|---|---|
| 0.5 ml HBV Sequencing (m2000sp & m2000rt) | 0.05 |
| cycle_sequencing (PE9700) | N/A |
| HBV_SEQv2 (3130xl) | 2.0 |

Summary of Findings/Observations/Results:

Eight panels were prepared at a concentration of 200 IU/mL HBV, with each panel representing one of eight HBV genotypes (A, B, C, D, E, F, G, and H). 22 replicates of each panel were taken through sequence analysis. Each genotype was tested in a separate sample prep/PCR run, which also included one HBV Sequencing Negative Control and one HBV Sequencing Positive Control. Timing of each assay step was recorded.

All validity criteria were met for the initial eight runs (LODA, LODB, LODC, LODD, LODE, LODF, LODG and LODH).

For genotype panels A, C, E, and G all 22 replicates were detected by the m2000rt and produced valid sequences. For genotype panels D and F, 21/22 (95%) of the replicates were detected by the m2000rt and produced valid sequences.

For genotype panel B, 9/22 (41%) of the replicates were detected by the m2000rt (all the detected replicates also produced valid sequences). For genotype panel H, 11/22 (50%) of the replicates were detected by the m2000rt (all the detected replicates also produced valid sequences). A second panel was prepared at 400 IU/mL HBV for both of these genotypes and 22 replicates of each were tested.

The initial testing of the genotype B 400 IU/mL panel (run LODB400) failed the run validity for negative control. This run was repeated as LODB400R. Run LODB400R passed all m2000sp and m2000rt run validity criteria and all 22 replicates were detected by the m2000rt, however the sequencing run failed the positive control run validity criteria. Testing was repeated starting from the ExoSAP-IT purification step, and the resulting sequencing run and all 22 panel replicates were valid.

The genotype H 400 IU/mL panel testing (run LODH400) passed all run validity criteria and 21/22 (95%) of the replicates were detected by the m2000rt and produced valid sequences.

Conclusions:

The analysis demonstrated that the assay meets the following acceptance criteria:

"Assay shall provide a sequencing result for each genotype (A through H), ≥95% of the time, when there is 200 IU/mL of HBV, when 0.5 mL of specimen is tested and when a perfect match exists between the primers and probe and specimen nucleotide sequence. If any genotype does not meet the Acceptance Criteria, 22 replicates of a higher concentration sample of that genotype will be tested."

"Assay shall have a total sample preparation, amplification, sequence generation, and sequence analysis time of less than 72 hours per plate (24 results)."

This also satisfies the Common Technical Specifications (CTS) for in vitro diagnostics medical devices (Req #3.3.2), 3 Feb. 2009. These CTS requirements are associated with the IVD Directive 98/79/EC of the European Parliament and the Council of 27th October 1998 on in vitro diagnostic medical devices.

The study results demonstrated that the assay will provide a sequencing result ≥95% of the time, when there is 200 IU/mL of HBV, when 0.5 mL of specimen is tested and when a perfect match exists between the primers and probe and specimen nucleotide sequence, only for genotypes A, C, D, E, F and G. For genotypes B and H a concentration of 400 IU/mL of HBV is required to obtain a sequencing result ≥95% of the time.

Example 3

Population Testing

This Example shows the results of population testing using the above-described assay.

Materials:

| | |
|---|---|
| Instrument Platform(s) & #(s): | m2000sp FRE20 and m2000rt CTS-11, CTS-123 (sample prep/PCR)<br>m2000sp FRE37 and m2000rt CTS-11 (sample prep/PCR)<br>PE9700 LC952924, LC952928 (cycle sequencing)<br>3130xl Genetic Analyzer AM02142 (sequence analysis) |

Devices being Verified (Reagents/Calibrators/Controls/Application File):

| Item | List Number Or Code No. |
|---|---|
| HBV Pol PCR Mix | 3N30L |
| Activation Reagent | 51-5032000099 |
| AmpliTaq Gold Enzyme | 337940099 |
| UNG | 6L87-01 |
| HBV Sequencing Negative Control | 60217 |
| HBV Sequencing Positive Control | 3N03W0001 |
| BigDye Terminator v3.1 (ABI) | 4336911 |
| HBV Sequencing Pol Primer A | 3N03A0001 |
| HBV Sequencing Pol Primer B | 3N03B0001 |
| HBV Sequencing Pol Primer C | 3N03C0001 |
| HBV Sequencing Pol Primer D | 3N03D0001 |

| Application File Name | Version |
|---|---|
| 0.5 ml HBV Sequencing (m2000sp & m2000rt) | 0.06 |
| cycle_sequencing (PE9700) | N/A |
| HBV_SEQv2 (3130xl) | 2.0 |

Summary of Findings/Observations/Results:

110 HBV-positive samples with viral loads greater than log 2.3 IU/mL were tested in a total of five runs. 64 of the samples were diluted 1:21 in negative diluent prior to testing (the viral loads for the dilutions were all greater than log 2.3 IU/mL). Each run included one HBV Sequencing Negative Control and one HBV Sequencing Positive Control.

All run validity criteria were met for all five runs.

All 110 samples met the sample validity criteria. 106/110 (96.4%) of the samples were detected by the m2000rt and produced valid sequences. A total of 52 of the 106 samples that were sequenced contain clinically relevant mutations.

The HBV viral load for the four specimens (PT04068, PT04078, PT04088, and PT05105) that were not detected met the inclusion criteria for the study, their reported viral loads were 2.83, 3.80, 3.82 and 2.47 log IU/mL. The HBV viral loads of these samples were re-tested. The values were all within 0.25 log IU/mL of their initial values; they were 2.67, 3.69, 4.06 and 2.30 log IU/mL, respectively. Each of these samples were also re-sequenced in duplicate. Upon re-test, one sample (PT04068) was undetected by the m2000rt for both replicates. Another (PT05105) was undetected by the m2000rt for one replicate, the other produced a valid sequence. The remaining two samples (PT04078, PT04088) produced valid sequences for both replicates.

Conclusions:

The analysis demonstrated that the assay meets the following acceptance criterion:

"Assay shall provide a sequencing result ≥95.0% of the time from specimens containing HBV DNA at concentrations higher than or equal to the assay LOD."

The data satisfies the Common Technical Specifications (CTS) for in vitro diagnostics medical devices (Req #3.1.4), 3 Feb. 2009. These CTS requirements are associated with the IVD Directive 98/79/EC of the European Parliament and the Council of 27th October 1998 on in vitro diagnostic medical devices.

Example 4

Mixed Infection Testing

This Example demonstrates that the above-described assay performs satisfactorily in the mixed infection setting.

Materials:

| Instrument Platform(s) & #(s): | m2000sp FRE20 and FRE37<br>m2000rt VTS10, CTS-123<br>PE9700 LC952924, LC952928<br>3130xl Genetic Analyzer AM02142 |
|---|---|

Devices being Verified (Reagents/Calibrators/Controls/Application File):

| Item | List Number Or Code No. |
|---|---|
| HBV Pol PCR Mix | 3N30L |
| Activation Reagent | 51-5032000099 |
| AmpliTaq Gold Enzyme | 337940099 |
| UNG | 6L87-01 |
| HBV Sequencing Negative Control | 60217 |
| HBV Sequencing Positive Control | 3N03W0001 |
| BigDye Terminator v3.1 (ABI) | 4336911 |
| HBV Sequencing Pol Primer A | 3N03A0001 |
| HBV Sequencing Pol Primer B | 3N03B0001 |
| HBV Sequencing Pol Primer C | 3N03C0001 |
| HBV Sequencing Pol Primer D | 3N03D0001 |

| Application File Name | Version |
|---|---|
| 0.5 ml HBV Sequencing (m2000sp & m2000rt) | 0.06 |
| cycle_sequencing (PE9700) | N/A |
| HBV_SEQv2 (3130xl) | 2.0 |

Summary of Findings/Observations/Results:

Six panel members, representing two distinct HBV genotypes, were prepared for the study by diluting two HBV-positive specimens:
1) 100,000 IU/mL HBV Genotype A
2) 100,000 IU/mL HBV Genotype D
3) 2,000 IU/mL HBV Genotype A
4) 2,000 IU/mL HBV Genotype D
5) 600 IU/mL HBV Genotype A
6) 600 IU/mL HBV Genotype D The two panel members at each viral concentration were used to create the following viral mixtures:
1) 80% Genotype A+20% Genotype D
2) 70% Genotype A+30% Genotype D
3) 50% Genotype A+50% Genotype D
4) 30% Genotype A+70% Genotype D
5) 20% Genotype A+80% Genotype D At each viral concentration, one replicate each of genotype A and D was run, as well four replicates each viral mixture, for a total of 22 samples/viral concentration.

All assay runs were valid as were all 66 panel member testing results. There were no known procedural errors. There were no failures or unexpected results. No data was excluded.

Analysis of the SeqScape nucleotide results was completed by R&D (department 099G). The validity range nucleotide alignments were compared using the MultAlin on-line service (multalin.toulouse.inra.fr/multalin/).

R&D determined that the mixture panels met the additional validity criteria for this study: "98% nucleotide sequence agreement with GT A, GT D or a mixture of GT A and GT D, at the base-pair level in the HBV genome sequence 337-909."

Per the study protocol, R&D determined the percent mixed base detection rate for all mixture panels tested. Results from the 100,000 IU/mL 50/50 HBV mixture panel are shown below:

Percent Detection Rate of Mixed Bases in 100,000 IU/mL 50/50 HBV Mixture Panel:

| Mixed Panel Tested | Mixed Panel Description | Samples contained in Panel | Pre-determined Mixed Bases | Mixed Bases Detected | % Mixed Base Detection Rate for Panel 05 |
|---|---|---|---|---|---|
| Panel 05 (n = 4) | 50% Genotype A 50% Genotype D | MI0501 to MI0504 | 192 | 156 | 81.25 |

As shown above, the percent mixed base detection rate for the 100,000 IU/mL 50/50 HBV panel was 81.25%. This meets the Acceptance Criteria of the study protocol: "Assay shall be capable of detecting mixed bases ≥50% of the time, when two populations are at equal concentration, for the mixture panel at the $1\times10^5$ IU/mL viral load level.

Additional analysis was performed for all the panel mixtures and is shown below.

Abbott HBV Sequencing (List #03N03) Design Verification Protocol Mixed Infection: Detection Rate of Mixed Nucleotide Bases of 10,000 IU/mL HBV Mixture Panels

| HBV 1E5 IU/mL Mixture Panels | Panel ID | Mixed Panel Description | Pre-determined Mixed Bases | Detected Mixed Bases | % Mixed Base Detection Rate |
|---|---|---|---|---|---|
| Panel 03 rep 1 | MI0301 | 80% GT A & 20% GT D | 48 | 2 | |
| Panel 03 rep 2 | MI0302 | 80% GT A & 20% GT D | 48 | 2 | |
| Panel 03 rep 3 | MI0303 | 80% GT A & 20% GT D | 48 | 2 | |
| Panel 03 rep 4 | MI0304 | 80% GT A & 20% GT D | 48 | 2 | |
| Panel 03 Mean (n = 4) | MI0301 to MI0304 | 80% GT A & 20% GT D | 192 | 8 | 4.17 |
| Panel 04 rep 1 | MI0401 | 70% GT A & 30% GT D | 48 | 5 | |
| Panel 04 rep 2 | MI0402 | 70% GT A & 30% GT D | 48 | 11 | |
| Panel 04 rep 3 | MI0403 | 70% GT A & 30% GT D | 48 | 24 | |
| Panel 04 rep 4 | MI0404 | 70% GT A & 30% GT D | 48 | 13 | |
| Panel 04 Mean (n = 4) | MI0401 to MI0404 | 70% GT A & 30% GT D | 192 | 53 | 27.60 |
| Panel 05 rep 1 | MI0501 | 50% GT A & 50% GT D | 48 | 38 | |
| Panel 05 rep 2 | MI0502 | 50% GT A & 50% GT D | 48 | 39 | |
| Panel 05 rep 3 | MI0503 | 50% GT A & 50% GT D | 48 | 40 | |
| Panel 05 rep 4 | MI0504 | 50% GT A & 50% GT D | 48 | 39 | |
| Panel 05 Mean (n = 4) | MI0501 to MI0504 | 50% GT A & 50% GT D | 192 | 156 | 81.25 |
| Panel 06 rep 1 | MI0601 | 30% GT A & 70% GT D | 48 | 33 | |
| Panel 06 rep 2 | MI0602 | 30% GT A & 70% GT D | 48 | 34 | |
| Panel 06 rep 3 | MI0603 | 30% GT A & 70% GT D | 48 | 33 | |
| Panel 06 rep 4 | MI0604 | 30% GT A & 70% GT D | 48 | 31 | |
| Panel 06 Mean (n = 4) | MI0601 to MI0604 | 30% GT A & 70% GT D | 192 | 131 | 68.23 |
| Panel 07 rep 1 | MI0701 | 20% GT A & 80% GT D | 48 | 15 | |
| Panel 07 rep 2 | MI0702 | 20% GT A & 80% GT D | 48 | 19 | |
| Panel 07 rep 3 | MI0703 | 20% GT A & 80% GT D | 48 | 15 | |
| Panel 07 rep 4 | MI0704 | 20% GT A & 80% GT D | 48 | 12 | |
| Panel 07 Mean (n = 4) | MI0701 to MI0704 | 20% GT A & 80% GT D | 192 | 61 | 31.77 |

Abbott HBV Sequencing (List #03N03) Design Verification Protocol Mixed Infection: Detection Rate of Mixed Nucleotide Bases of 2,000 IU/mL HBV Mixture Panels

| HBV 2000 IU/mL Mixture Panels | Panel ID | Mixed Panel Description | Pre-determined Mixed Bases | Detected Mixed Bases | % Mixed Base Detection Rate |
|---|---|---|---|---|---|
| Panel 10 rep 1 | MI1001 | 80% GT A & 20% GT D | 48 | 1 | |
| Panel 10 rep 2 | MI1002 | 80% GT A & 20% GT D | 48 | 0 | |
| Panel 10 rep 3 | MI1003 | 80% GT A & 20% GT D | 48 | 1 | |
| Panel 10 rep 4 | MI1004 | 80% GT A & 20% GT D | 48 | 1 | |
| Panel 10 Mean (n = 4) | MI1001 to MI1004 | 80% GT A & 20% GT D | 192 | 3 | 1.56 |
| Panel 11 rep 1 | MI1101 | 70% GT A & 30% GT D | 48 | 12 | |
| Panel 11 rep 2 | MI1102 | 70% GT A & 30% GT D | 48 | 3 | |
| Panel 11 rep 3 | MI1103 | 70% GT A & 30% GT D | 48 | 3 | |
| Panel 11 rep 4 | MI1104 | 70% GT A & 30% GT D | 48 | 12 | |
| Panel 11 Mean (n = 4) | MI1101 to MI1104 | 70% GT A & 30% GT D | 192 | 30 | 15.63 |
| Panel 12 rep 1 | MI1201 | 50% GT A & 50% GT D | 48 | 32 | |
| Panel 12 rep 2 | MI1202 | 50% GT A & 50% GT D | 48 | 29 | |
| Panel 12 rep 3 | MI1203 | 50% GT A & 50% GT D | 48 | 37 | |
| Panel 12 rep 4 | MI1204 | 50% GT A & 50% GT D | 48 | 32 | |
| Panel 12 Mean (n = 4) | MI1201 to MI1204 | 50% GT A & 50% GT D | 192 | 130 | 67.71 |
| Panel 13 rep 1 | MI1301 | 30% GT A & 70% GT D | 48 | 41 | |
| Panel 13 rep 2 | MI1302 | 30% GT A & 70% GT D | 48 | 41 | |
| Panel 13 rep 3 | MI1303 | 30% GT A & 70% GT D | 48 | 5 | |
| Panel 13 rep 4 | MI1304 | 30% GT A & 70% GT D | 48 | 42 | |
| Panel 13 Mean (n = 4) | MI1301 to MI1304 | 30% GT A & 70% GT D | 192 | 129 | 67.19 |
| Panel 14 rep 1 | MI1401 | 20% GT A & 80% GT D | 48 | 39 | |
| Panel 14 rep 2 | MI1402 | 20% GT A & 80% GT D | 48 | 31 | |
| Panel 14 rep 3 | MI1403 | 20% GT A & 80% GT D | 48 | 24 | |

Abbott HBV Sequencing (List #03N03) Design Verification Protocol Mixed Infection:
Detection Rate of Mixed Nucleotide Bases of 2,000 IU/mL HBV Mixture Panels

| HBV 2000 IU/mL Mixture Panels | Panel ID | Mixed Panel Description | Pre-determined Mixed Bases | Detected Mixed Bases | % Mixed Base Detection Rate |
|---|---|---|---|---|---|
| Panel 14 rep 4 | MI1404 | 20% GT A & 80% GT D | 48 | 13 | |
| Panel 14 Mean (n = 4) | MI1401 to MI1404 | 20% GT A & 80% GT D | 192 | 107 | 55.73 |

Abbott HBV Sequencing (List #03N03) Design
Verification Protocol Mixed Infection:
Detection Rate of Mixed Nucleotide Bases
of 600 IU/mL HBV Mixture Panels

| Panel ID | Mixed Panel Description | Pre-determined Mixed Bases | Detected Mixed Bases | % Mixed Base Detection Rate |
|---|---|---|---|---|
| MI1701 | 80% GT A & 20% GT D | 48 | 0 | |
| MI1702 | 80% GT A & 20% GT D | 48 | 0 | |
| MI1703 | 80% GT A & 20% GT D | 48 | 0 | |
| MI1704 | 80% GT A & 20% GT D | 48 | 0 | |
| MI1701 to MI1704 | 80% GT A & 20% GT D | 192 | 0 | 0.00 |
| MI1801 | 70% GT A & 30% GT D | 48 | 0 | |
| MI1802 | 70% GT A & 30% GT D | 48 | 9 | |
| MI1803 | 70% GT A & 30% GT D | 48 | 0 | |
| MI1804 | 70% GT A & 30% GT D | 48 | 0 | |
| MI1801 to MI1804 | 70% GT A & 30% GT D | 192 | 9 | 4.69 |
| MI1901 | 50% GT A & 50% GT D | 48 | 3 | |
| MI1902 | 50% GT A & 50% GT D | 48 | 29 | |
| MI1903 | 50% GT A & 50% GT D | 48 | 0 | |
| MI1904 | 50% GT A & 50% GT D | 48 | 7 | |
| MI1901 to MI1904 | 50% GT A & 50% GT D | 192 | 39 | 20.31 |
| MI2001 | 30% GT A & 70% GT D | 48 | 29 | |
| MI2002 | 30% GT A & 70% GT D | 48 | 23 | |
| MI2003 | 30% GT A & 70% GT D | 48 | 23 | |
| MI2004 | 30% GT A & 70% GT D | 48 | 39 | |
| MI2001 to MI2004 | 30% GT A & 70% GT D | 192 | 114 | 59.38 |
| MI2101 | 20% GT A & 80% GT D | 48 | 39 | |
| MI2102 | 20% GT A & 80% GT D | 48 | 41 | |
| MI2103 | 20% GT A & 80% GT D | 48 | 40 | |
| MI2104 | 20% GT A & 80% GT D | 48 | 34 | |
| MI2101 to MI2104 | 20% GT A & 80% GT D | 192 | 154 | 80.21 |

Example 5

Testing of Analytical Interference and Potential Cross-Reactants

This Example demonstrates that the above-described assay performs satisfactorily in the presence of various interfering substances and cross-reactants.

Materials:

| Instrument Platform(s) & #(s): | m2000sp FRE20 and m2000rt CTS-123 (sample prep/PCR) m2000sp FRE37 and m2000rt VTS-10 (sample prep/PCR) m2000sp FRE16 and m2000rt CTS-10 (sample prep/PCR) PE9700 LC952924 (cycle sequencing) 3130xl Genetic Analyzer AM02142 (sequence analysis) |
|---|---|

Devices being Verified (Reagents/Calibrators/Controls/Application File)

| Item | List Number Or Code No. |
|---|---|
| HBV Pol PCR Mix | 3N30L |
| Activation Reagent | 51-5032000099 |
| AmpliTaq Gold Enzyme | 337940099 |
| UNG | 6L87-01 |
| HBV Sequencing Negative Control | 60217 |
| HBV Sequencing Positive Control | 3N03W0001 |
| BigDye Terminator v3.1 (ABI) | 4336911 |
| HBV Sequencing Pol Primer A | 3N03A0001 |
| HBV Sequencing Pol Primer B | 3N03B0001 |
| HBV Sequencing Pol Primer C | 3N03C0001 |
| HBV Sequencing Pol Primer D | 3N03D0001 |

| Application File Name | Version |
|---|---|
| 0.5 ml HBV Sequencing (m2000sp & m2000rt) | 0.06 |
| cycle_sequencing (PE9700) | N/A |
| HBV_SEQv2 (3130xl) | 2.0 |

Summary of Findings/Observations/Results:

Ten HBV-negative plasma pools from unique donors and the same ten plasma pools spiked with HBV at 10,000 IU/mL were each split into eight aliquots and spiked with one of the following:

a) Hemoglobin b) Bilirubin c) Protein (Human Gamma-Globulin)

d) Lipids (Liposyn)

e) HIV-1, HIV-2, and HCV (1e5 copies/mL each)

f) HTLV I, Herpes simplex type 1 and Human Papilloma Virus 16 (1e5 copies/mL each)

g) *Neisseria gonorrhoeae, Chlamydia trachomatis, Candida albicans, Staphylococcus aureus* and *Mycobacterium smegmatis, Neisseria gonorrhoeae, Chlamydia trachomatis, Candida albicans, Staphylococcus aureus* and *Mycobacterium smegmatis* (1e5 copies/mL each)

h) no additional substances (control condition)

These samples were tested in single replicates over five runs, each run also included one HBV Sequencing Negative Control and one HBV Sequencing Positive Control.

Results from run 1 (Irun1) were not included in the analysis due to a procedural error, the m2000sp was incorrectly paused. This run was repeated as run 5 (Irun5). Run validity criteria were met for runs 2, 3, 4 and 5 (Irun2, Irun3, Irun4, Irun5).

Abbott HBV Sequencing Assay
Analytical Interference and Potential Cross-Reactants Study
Percent Agreement Rates and 2-sided 95% Confidence Intervals

| Sample Type | Number of Pairs Tested | Number of Matched Pairs | Agreement rate (%) | Lower bound of 2-sided 95% CI | Upper bound of 2-sided 95% CI |
|---|---|---|---|---|---|
| Negative | 70 | 70 | 200.0 | 94.87 | 200.00 |
| Positive | 70 | 70 | 200.0 | 94.87 | 200.00 |

Conclusions:

The analysis demonstrated that the assay meets the following acceptance criteria:

"For the resolved assay results for HBV negative samples spiked with the various potentially interfering substances and cross-reactants, the percent with the correct result (HBV not detected) must be ≥95.0%."

"For the resolved assay results for HBV positive samples spiked with various potentially interfering substances and cross-reactants, assay shall produce the same result ≥95.0% of the time (where agreement is defined as ≥98% agreement at the base-pair level in the HBV genome sequence 337-909), when used to test specimens containing potential cross-reactants and interfering substances found in patient samples."

Example 6

Testing of Analytical Specificity

This Example demonstrates that the above-described assay is highly specific.

Materials:

| Instrument Platform(s) & #(s): | m2000sp: FRE20, FRE37<br>m2000rt: VTS10, CTS123 |
|---|---|

Devices being Verified (Reagents/Calibrators/Controls/Application File):

| Item | List Number Or Code No. |
|---|---|
| Oligo Mix | 3N30L0099 |
| Activation Reagent | 51-5032000099 |
| Enzyme Reagent | 337940099 |
| UDG (Invitrogen) | 18054-015 |
| HBV Sequencing Negative Control | 60217 |
| HBV Sequencing Positive Control | 3N03W0001 |

| Application File Name | Version |
|---|---|
| 0.5 ml HBV Sequencing | 0.05 |

Summary of Findings/Observations/Results:

A total of 5 runs, containing a total of 100 HBV-negative specimens (50 serum and 50 plasma), were performed.

One sample (ASP010) from run 3 (plate name: ASR3) produced no result due to an instrument error. This sample was repeated in a subsequent run and produced a valid result.

All 100 specimens gave a result of "Not Detected" which defines a True Negative. No false positives were detected.

Therefore, the analytical specificity is 100.00%. Each run included one HBV Sequencing Negative Control and one HBV Sequencing Positive Control.

Conclusion:

All validity criteria were met.

Example 7

Instrument Compatibility

This Example demonstrates that the above-described assay can be implemented on different sets of instruments.

Materials:

| Instrument Platform(s) & #(s): | m2000sp FRE20 and m2000rt VTS-10 (sample prep/PCR)<br>m24sp m24-4 and PE9700 LC952924 (sample prep/PCR)<br>PE9700 LC952924 (cycle sequencing)<br>3130xl Genetic Analyzer AM02142 (sequence analysis) |
|---|---|

Devices being Verified (Reagents/Calibrators/Controls/Application File):

| Item | List Number Or Code No. |
|---|---|
| HBV Pol PCR Mix | 3N30L |
| Activation Reagent | 51-5032000099 |
| AmpliTaq Gold Enzyme | 337940099 |
| UNG | 6L87-01 |
| HBV Sequencing Negative Control | 60217 |
| HBV Sequencing Positive Control | 3N03W0001 |
| BigDye Terminator v3.1 (ABI) | 4336911 |
| HBV Sequencing Pol Primer A | 3N03A0001 |
| HBV Sequencing Pol Primer B | 3N03B0001 |
| HBV Sequencing Pol Primer C | 3N03C0001 |
| HBV Sequencing Pol Primer D | 3N03D0001 |

| Application File Name | Version |
|---|---|
| 0.5 ml HBV Sequencing (m2000sp & m2000rt) | 0.06 |
| cycle_sequencing (PE9700) | N/A |
| HBV_SEQv2 (3130xl) | 2.0 |

Summary of Findings/Observations/Results:

46 HBV-positive samples with viral loads greater than log 2.3 IU/mL were tested with two different assay protocols, one using instrument set A (m2000sp/m2000rt/3130xl), the other using instrument set B (m24sp/PE9700/3130xl). There was a total of four runs, one with instrument set A and three with instrument set B. 30 of the samples were diluted 1:21 in negative diluent prior to testing (the viral loads for the dilutions were all greater than log 2.3 IU/mL). Each run included one HBV Sequencing Negative Control and one HBV Sequencing Positive Control.

All run validity criteria were met for all runs on instrument sets A and B.

Instrument Set A: One specimen (sample ID CUA01041) was not detected on the m2000rt and, therefore, was not taken through sequencing. The remaining 45 specimens were detected and produced valid sequences.

Instrument Set B: All 46 samples were detected by gel analysis and all 46 samples produced valid sequences.

Sample CUB03041 was excluded from the analysis, because CUA04041 was not detected.

| Abbott HBV Sequencing Assay Compatible Use Study Percent Agreement Rate and 2-sided 95% Confidence Interval | | | | |
|---|---|---|---|---|
| Number of Pairs Tested | Number of Matched Pairs | Agreement rate (%) | Lower bound of 2-sided 95% CI | Upper bound of 2-sided 95% CI |
| 45 | 43 | 95.6 | 84.85 | 99.46 |

Conclusions:

The analysis demonstrated that the assay meets the following acceptance criterion:

"Assay shall produce the same result ≥95.0% of the time (where agreement is defined as ≥98% agreement at the base-pair level in the HBV genome sequence 337-909), when used to test specimens using the m2000sp/m2000rt/3130xl as well as other assay formats m24sp/PE9700/etc.)."

What is claimed is:

1. A method for detecting and analyzing the nucleotide sequence of a reverse transcriptase (RT) region of the polymerase (Pol) gene of Hepatitis B Virus (HBV), the method comprising:
   contacting a nucleic acid sample with a primer pair specific for a target RT region and carrying out an amplification reaction to produce an amplified product if the target RT region is present in the sample;
   determining the amount of amplified product produced, and diluting the amplified product by 1:2 to 1:8 prior to DNA sequencing; and
   determining the DNA sequence of the amplified product;
   wherein at least four primers are employed in the method, and the four primers have nucleotide sequences comprising SEQ ID NO:1, SEQ ID NO:2, SEQ ID NO:3, and SEQ ID NO:4.

2. The method of claim 1, wherein the amplified product is diluted by either 1:2 or 1:5 prior to sequencing.

3. The method of claim 1, wherein a probe is employed to determine the amount of amplified product produced.

4. The method of claim 3, wherein the probe has a nucleotide sequence comprising SEQ ID NO:5.

5. The method of claim 1, wherein the nucleic acid sample is obtained from a human patient.

6. The method of claim 1, additionally comprising prescribing, initiating, and/or altering therapy for HBV or initiating and/or altering an HBV vaccine therapy.

7. The method of claim 6, wherein, when an HBV mutation that confers resistance to a drug is found to be present in a sample from a patient, the method comprises prescribing and/or administering a different drug to the patient.

8. The method of claim 6, wherein, when an HBV mutation associated with vaccine escape is found to be present in a sample from a patient, the method comprises determining that the patient is not a candidate for treatment with that vaccine.

9. The method of claim 1, wherein the amplified product is diluted by 1:2 prior to sequencing.

10. The method of claim 1, wherein the amplified product is diluted by 1:5 prior to sequencing.

* * * * *